(12) United States Patent
Dong et al.

(10) Patent No.: US 7,792,394 B2
(45) Date of Patent: Sep. 7, 2010

(54) PHOTONIC BANDGAP FIBERS

(75) Inventors: Liang Dong, Ann Arbor, MI (US); Xiang Peng, Ann Arbor, MI (US)

(73) Assignee: IMRA America, Inc., Ann Arbor, MI (US)

( * ) Notice: Subject to any disclaimer, the term of this patent is extended or adjusted under 35 U.S.C. 154(b) by 0 days.

(21) Appl. No.: 12/188,153

(22) Filed: Aug. 7, 2008

(65) Prior Publication Data

US 2009/0122308 A1    May 14, 2009

Related U.S. Application Data

(62) Division of application No. 11/686,810, filed on Mar. 15, 2007, now Pat. No. 7,418,836, which is a division of application No. 11/323,177, filed on Dec. 30, 2005, now Pat. No. 7,209,619.

(60) Provisional application No. 60/640,345, filed on Dec. 30, 2004.

(51) Int. Cl.
*G02B 6/00* (2006.01)
*G01J 3/44* (2006.01)
*G01J 3/00* (2006.01)
*H04J 14/02* (2006.01)
*G01N 31/00* (2006.01)

(52) U.S. Cl. ............... 385/12; 385/123; 385/122; 385/125; 385/126; 385/127; 356/301; 356/300; 398/79; 703/24

(58) Field of Classification Search ............ 385/12, 385/14, 122, 123, 124, 125, 126, 127, 128, 385/141; 356/301, 300, 437; 398/79, 92, 398/151; 702/24

See application file for complete search history.

(56) References Cited

U.S. PATENT DOCUMENTS

| 4,641,917 | A |   | 2/1987 | Glodis |
|-----------|---|---|--------|--------|
| 4,784,486 | A | * | 11/1988 | Van Wagenen et al. ...... 356/301 |
| 5,032,001 | A |   | 7/1991 | Shang |
| 5,121,460 | A |   | 6/1992 | Tumminelli |

(Continued)

FOREIGN PATENT DOCUMENTS

CN    1686884    10/2005

(Continued)

OTHER PUBLICATIONS

P. Yeh, et al.: "Theory of Bragg Fiber", J. Opt. Soc. Am., vol. 68, No. 9, Sep. 1978, pp. 1196-1201.

(Continued)

*Primary Examiner*—Brian M Healy
(74) *Attorney, Agent, or Firm*—Knobbe Martens Olson & Bear LLP

(57) ABSTRACT

Included among the many structures described herein are photonic bandgap fibers designed to provide a desired dispersion spectrum. Additionally, designs for achieving wide transmission bands and lower transmission loss are also discussed. For example, in some fiber designs, smaller dimensions of high index material in the cladding and large core size provide small flat dispersion over a wide spectral range. In other examples, the thickness of the high index ring-shaped region closest to the core has sufficiently large dimensions to provide negative dispersion or zero dispersion at a desired wavelength. Additionally, low index cladding features distributed along concentric rings or circles may be used for achieving wide bandgaps.

14 Claims, 35 Drawing Sheets

U.S. PATENT DOCUMENTS

| | | | |
|---|---|---|---|
| 5,175,785 A | 12/1992 | Dabby | |
| 5,353,363 A | 10/1994 | Keck | |
| 5,452,394 A | 9/1995 | Huang | |
| 5,521,703 A * | 5/1996 | Mitchell | 356/301 |
| 5,615,673 A | 4/1997 | Berger et al. | 128/633 |
| 5,742,722 A | 4/1998 | Imoto | |
| 5,802,236 A | 9/1998 | DiGiovanni | 385/127 |
| 5,818,630 A | 10/1998 | Fermann et al. | |
| 6,072,811 A | 6/2000 | Fermann et al. | |
| 6,236,779 B1 | 5/2001 | Kafka | |
| 6,243,522 B1 | 6/2001 | Allan | 385/123 |
| 6,334,017 B1 | 12/2001 | West | 385/123 |
| 6,334,019 B1 | 12/2001 | Birks et al. | 385/125 |
| 6,389,198 B2 | 5/2002 | Kafka | |
| 6,418,258 B1 | 7/2002 | Wang | 385/125 |
| 6,444,133 B1 | 9/2002 | Fajardo et al. | 216/24 |
| 6,542,681 B2 * | 4/2003 | Broeng et al. | 385/123 |
| 6,631,234 B1 | 10/2003 | Russell | |
| 6,652,163 B2 | 11/2003 | Fajardo | 385/96 |
| 6,778,732 B1 | 8/2004 | Fermann et al. | |
| 6,792,188 B2 | 9/2004 | Libori | |
| 6,795,635 B1 | 9/2004 | Fajardo et al. | 385/140 |
| 6,825,974 B2 | 11/2004 | Kliner et al. | |
| 6,836,607 B2 | 12/2004 | Dejneka et al. | |
| 6,845,204 B1 * | 1/2005 | Broeng et al. | 385/126 |
| 6,853,786 B2 | 2/2005 | Russell | |
| 6,856,742 B2 | 2/2005 | Broeng et al. | 385/125 |
| 6,888,992 B2 | 5/2005 | Russell | 385/125 |
| 6,892,018 B2 | 5/2005 | Libori et al. | 385/127 |
| 6,954,574 B1 | 10/2005 | Russell | |
| 6,972,894 B2 | 12/2005 | Bjarklev | |
| 6,987,783 B2 | 1/2006 | Fajardo | |
| 6,990,282 B2 | 1/2006 | Russell | |
| 7,054,513 B2 | 5/2006 | Herz et al. | 385/12 |
| 7,106,932 B2 | 9/2006 | Birks | |
| 7,116,875 B2 | 10/2006 | Wadsworth | |
| 7,136,558 B2 | 11/2006 | Epworth et al. | 385/123 |
| 7,155,097 B2 | 12/2006 | Jakobsen | |
| 7,174,078 B2 | 2/2007 | Libori | |
| 7,209,619 B2 | 4/2007 | Dong et al. | 385/127 |
| 7,221,840 B2 | 5/2007 | Vienne | |
| 7,224,873 B2 | 5/2007 | Bird | |
| 7,245,807 B2 | 7/2007 | Mangan | |
| 7,257,302 B2 | 8/2007 | Fermann | |
| 7,266,275 B2 | 9/2007 | Hansen | |
| 7,280,730 B2 | 10/2007 | Dong et al. | |
| 7,304,309 B2 * | 12/2007 | Suhami | 250/370.11 |
| 7,305,164 B2 | 12/2007 | Williams | |
| 7,321,712 B2 | 1/2008 | Williams | |
| 7,327,922 B2 | 2/2008 | Skovgaard | |
| 7,346,249 B2 | 3/2008 | Russell | |
| 7,349,611 B2 | 3/2008 | Broeng | |
| 7,414,780 B2 | 8/2008 | Fermann | |
| 7,418,836 B2 * | 9/2008 | Dong et al. | 65/393 |
| 7,532,798 B2 | 5/2009 | Williams | |
| 7,539,382 B2 | 5/2009 | Skovgaard | |
| 7,590,323 B2 | 9/2009 | Broeng | |
| 2001/0024546 A1 | 9/2001 | Kafka | |
| 2002/0159736 A1 | 10/2002 | Dejneka | |
| 2002/0181534 A1 | 12/2002 | Hodgson | |
| 2003/0059185 A1 | 3/2003 | Russell | |
| 2004/0005127 A1 | 1/2004 | Kliner | |
| 2004/0033043 A1 | 2/2004 | Monro et al. | 385/125 |
| 2004/0052484 A1 | 3/2004 | Broeng et al. | 385/125 |
| 2004/0071423 A1 | 4/2004 | Libori et al. | 385/127 |
| 2004/0146264 A1 * | 7/2004 | Auner et al. | 385/130 |
| 2004/0175084 A1 | 9/2004 | Broeng et al. | 385/125 |
| 2004/0213302 A1 | 10/2004 | Fermann et al. | 372/6 |
| 2004/0228592 A1 | 11/2004 | Gaeta | 385/125 |
| 2004/0258381 A1 | 12/2004 | Borrelli | 385/125 |
| 2005/0018714 A1 | 1/2005 | Fermann et al. | |
| 2005/0041702 A1 | 2/2005 | Fermann et al. | |
| 2005/0069269 A1 | 3/2005 | Libori | |
| 2005/0105865 A1 | 5/2005 | Fermann et al. | |
| 2005/0157998 A1 | 7/2005 | Dong et al. | 385/126 |
| 2005/0169590 A1 | 8/2005 | Alkeskjold | |
| 2005/0185908 A1 | 8/2005 | Roberts et al. | 385/125 |
| 2005/0226278 A1 | 10/2005 | Gu et al. | |
| 2005/0232313 A1 | 10/2005 | Fermann | |
| 2005/0238070 A1 | 10/2005 | Imeshev | |
| 2005/0276556 A1 | 12/2005 | Williams et al. | 385/123 |
| 2006/0005579 A1 | 1/2006 | Jacobsen | |
| 2006/0067632 A1 | 3/2006 | Broeng | |
| 2006/0177187 A1 | 8/2006 | Williams | |
| 2006/0193583 A1 | 8/2006 | Dong et al. | |
| 2006/0209908 A1 | 9/2006 | Pedersen | |
| 2006/0263024 A1 | 11/2006 | Dong et al. | 385/125 |
| 2007/0163301 A1 | 7/2007 | Dong et al. | 65/393 |
| 2007/0201801 A1 | 8/2007 | Provost | |
| 2009/0122308 A1 * | 5/2009 | Dong et al. | 356/301 |
| 2009/0257055 A1 * | 10/2009 | Chen et al. | 356/301 |

FOREIGN PATENT DOCUMENTS

| | | | |
|---|---|---|---|
| DE | 60004638 | 6/2004 | |
| EP | 1043281 | 10/2000 | |
| EP | 1421420 | 1/2007 | |
| FR | 2333628 | 7/1977 | |
| GB | 2103202 | 2/1983 | |
| JP | 5345632 | 12/1993 | |
| JP | 6037385 | 2/1994 | |
| JP | 6298542 | 10/1994 | |
| JP | 2002116181 | 4/2002 | |
| WO | WO 9836300 | 8/1998 | |
| WO | WO 00/16141 | 3/2000 | 385/125 X |
| WO | WO 00/49435 | 8/2000 | |
| WO | WO 00/60390 | 10/2000 | |
| WO | WO 01/37008 | 5/2001 | 385/125 X |
| WO | WO 02/088801 | 11/2002 | |
| WO | WO 02/101429 | 12/2002 | |
| WO | WO 03/078338 | 9/2003 | |
| WO | WO 03/100488 | 12/2003 | |
| WO | WO 2004/019092 | 3/2004 | |
| WO | WO 2004/053550 | 6/2004 | |
| WO | WO 2004/111695 | 12/2004 | |
| WO | WO 2005/041367 | 5/2005 | |
| WO | WO 2005/059612 | 6/2005 | |
| WO | WO 2005054139 | 6/2005 | |
| WO | WO 2005/091029 | 9/2005 | |
| WO | WO 2006/005111 | 1/2006 | 385/12 X |
| WO | WO 2006112071 | 10/2006 | |

OTHER PUBLICATIONS

R.F. Cregan, et al.: "Single-Mode Photonic Band Gap Guidance of Light in Air", Science, vol. 285, Sep. 1999, pp. 1537-1539.

Y. Fink, et al.: "Guiding Optical Light in Air Using an All-Dielectric Structure", Journal of Lightwave Technology, vol. 17, No. 11, Nov. 1999, pp. 2039-2041.

G. Ouyang, et al.: "Comparative study of air-core and coaxial Bragg fibers: single-mode transmission and dispersion characteristics", Optics Express, vol. 9, No. 13, 2001, pp. 733-747.

G. Ouyang, et al.: "Theoretical study on dispersion compensation in air-core Bragg fibers", Optics Express, vol. 10, No. 17, 2002, pp. 899-908.

D.G. Ouzounov, et al.: "Generation of Megawatt Optical Solitons in Hollow-Core Photonic Band-Gap Fibers", Science vol. 301, Sep. 19, 2003, pp. 1702-1704.

J. A. Monsoriu, et al., "High-index-core Bragg fibers: dispersion properties", Optics Express, vol. 11, No. 12, 2003, pp. 1400-1405.

G. Bouwmans, et al., "Properties of a hollow-core photonic bandgap fiber at 850 nm wavelength", Optic Express, vol. 11, No. 14, 2003, pp. 1613-1620.

J. Lægsaard, et al., "Material effect in air-guiding photonic bandgap fibers", Journal of the Optical Society of America B, vol. 20, No. 10, 2003, pp. 2046-2051.

T.G. Engeness, et al., "Dispersion tailoring and compensation by modal interaction in OmniGuide fibers", Optics Express, vol. 11, No. 10, 2003, 1175-1196.

B,J, Mangan, et al., "Low loss (1.7 dB/km) hollow core photonic bandgap fiber", PDP24, Optical Communications Conference, Feb. 2004.

Smith, et al., "Low-loss hollow-core silica/air photonic bandgap fiber", Nature, vol. 424, Aug. 2004, pp. 657-659.

Ranka et al., "Visible continuum generation in air-silica microstructure optical fibers with anomalous dispersion at 800 nm," Optics Letters, vol. 25, No. 1, pp. 25-27, Jan. 2000.

Ranka et al., "Optical properties of high-delta air silica microstructure optical fibers," Optics Letters, vol. 25, No. 11, pp. 796-798, Jun. 2000.

J. M. Fini, "Design of solid and microstructure fibers for suppression of higher-order modes," Optics Express, vol. 13, No. 9, pp. 3477-3490, May 2, 2005.

T. Hasegawa, et al., "Hole-assisted lightguide fiber for large anomalous dispersion and low optical loss," Optics Express, vol. 9, No. 13, pp. 681-686, Dec. 17, 2001.

C. J. S. De Matos et al., "All-fiber chirped pulse amplification using highly-dispersive air-core photonic bandgap fiber," Optics Express vol. 11, No. 22, Nov. 3, 2003, pp. 2832-2837.

Office Action issued Jan. 25, 2010 for German Patent Application No. DE 10 2006 023 976.8.

Bouwmans, et al., "High-power Er:Yb fiber laser with very high numerical aperture pump-cladding waveguide", Applied Physics Letters, vol. 83, No. 5, pp. 817-818, Aug. 4, 2003.

Glas, et al., "Cladding pumped large-mode-area Nd-doped holey fiber laser", Optics Express, vol. 10, No. 6, pp. 286-290, Mar. 25, 2002.

Folkenberg, et al., "Experimental investigation of cutoff phenomena in nonlinear photonic crystal fibers", Optics Letters, vol. 28, No. 20, pp. 1882-1884, Oct. 15, 2003.

K. Furusawa, et al., "Cladding pumped Ytterbium-doped fiber laser with holey inner and outer cladding", Optics Express, vol. 9, No. 13, pp. 714-720, Dec. 17, 2001.

Kuhlmey, et al., "Microstructured Optical Fibers: wher's the edge?", Optics Express, vol. 10, No. 22, pp. 1285-1290, Nov. 4, 2002.

Kuhlmey, et al., "Modal cutoff in microstructured optical fibers", Optics Letters, vol. 27, No. 19 pp. 1684-1686, Oct. 1, 2002.

Mortensen, et al., "Improved large-mode-area endlessly single-mode photonic crystal fibers", Optics Letters, vol. 28, No. 6, pp. 393-395, Mar. 15, 2003.

Russell, et al., "Photonic Crystal Fibers", Science Mag. vol. 299, pp. 358-362, Jan. 17, 2003.

W. Wong, et al.; "Robust Single-Mode Propagation in Optical Fibers with Record Effective Areas", Conference on Lasers and Electro-Optics (CLEO), May 22-27, 2005, CLEO 05 CPDB10.

Knight, et. al., All-silica single-mode optical fiber with photonic crystal cladding, Oct. 1, 1996, vol. 21, No. 19, Optics Letters, pp. 1547-1549.

Birks, et. al., Endlessly single-mode photonic crystal fiber, Jul. 1, 1997, vol. 22, No. 13, Optics Letters, pp. 961-963.

J. A. Monsoriu, et al., "High-index-core Bragg fibers: dispersion properties", Optics Express, vol. 11, No. 12, 2003, pp. 1400-1405.

International Search Report and Written Opinion in International Application No. PCT/US2008/074668 dated Jan. 27, 2009.

Galvanauskas, Mode-scalable fiber chirped pulse amplification systems, IEEE J. Sel. Top. Quantum Electronics, vol. 7, No. 4, pp. 504-517 (2001).

Knight, Properties of photonic crystal fiber and the effective index model, J. Opt. Soc Am. A/Vol. 15, No. 3/Mar. 1998 pp. 748-752.

Limpert, et al., "High power air-clad large-mode-area photonic crystal fiber laser", Optics Express, vol. 11, pp. 818-823, 2003.

Limpert, et al., High power Q-switched Yb-doped photonic crystal fiber laser producing sub-10 pulses, Conf. on Advanced Solid State Photonics, paper PD-411, Vienna (2005).

Martinez, et al., (E)ESI determination from mode-field diameter and refractive index profile measurements on single-mode fibers, IEE Proceedings V135, pp. 202-210, (1988).

Mortenson, Modal cutoff and the V parameter in photonic crystal fibers, Optics Letters vol. 28, No. 20 p. 1879-1881, Oct. 15, 2003.

N. Deguil-Robin, et al., Rod-type fiber laser, Advanced Solid State Photonics, 2005.

International Search Report and Written Opinion in International Application No. PCT/US05/00911 dated Jul. 18, 2006.

International Search Report and Written Opinion in International Application No. PCT/US05/47520 dated Jan. 23, 2007.

* cited by examiner

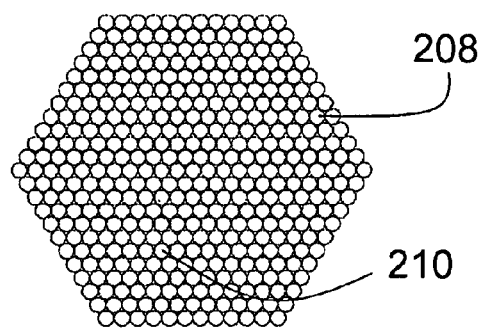
Figure 2F
Figure 3A
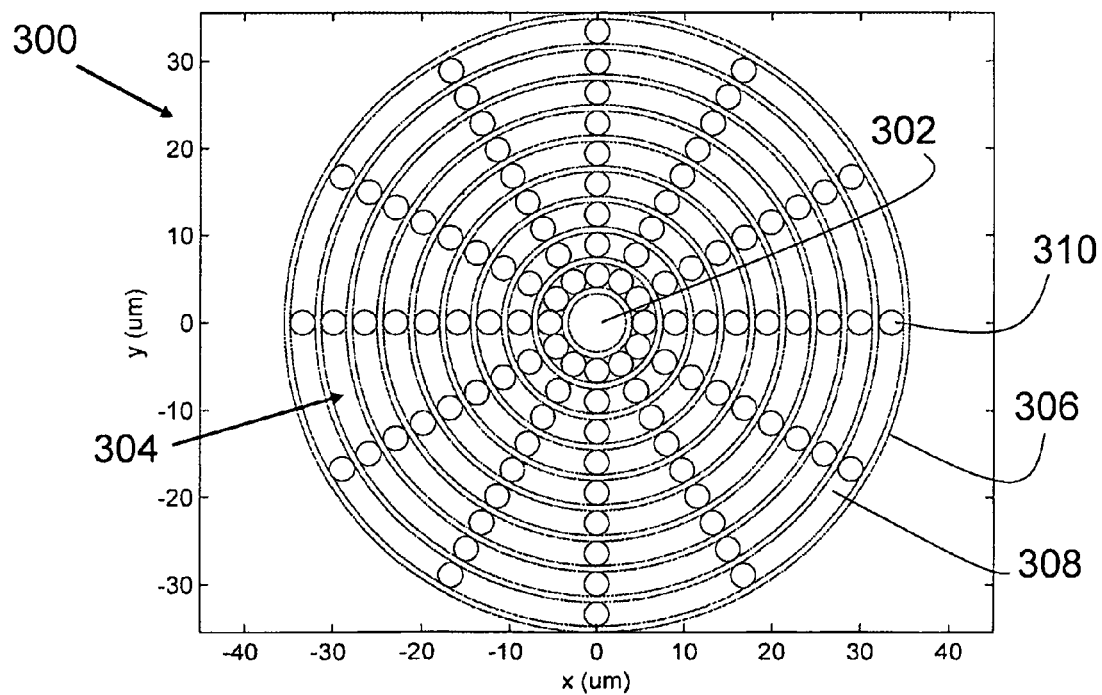

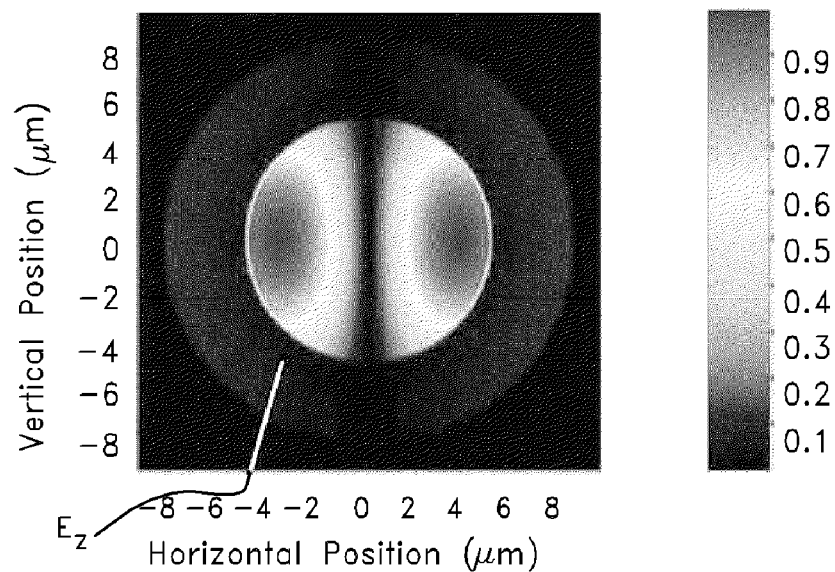
Figure 7A1

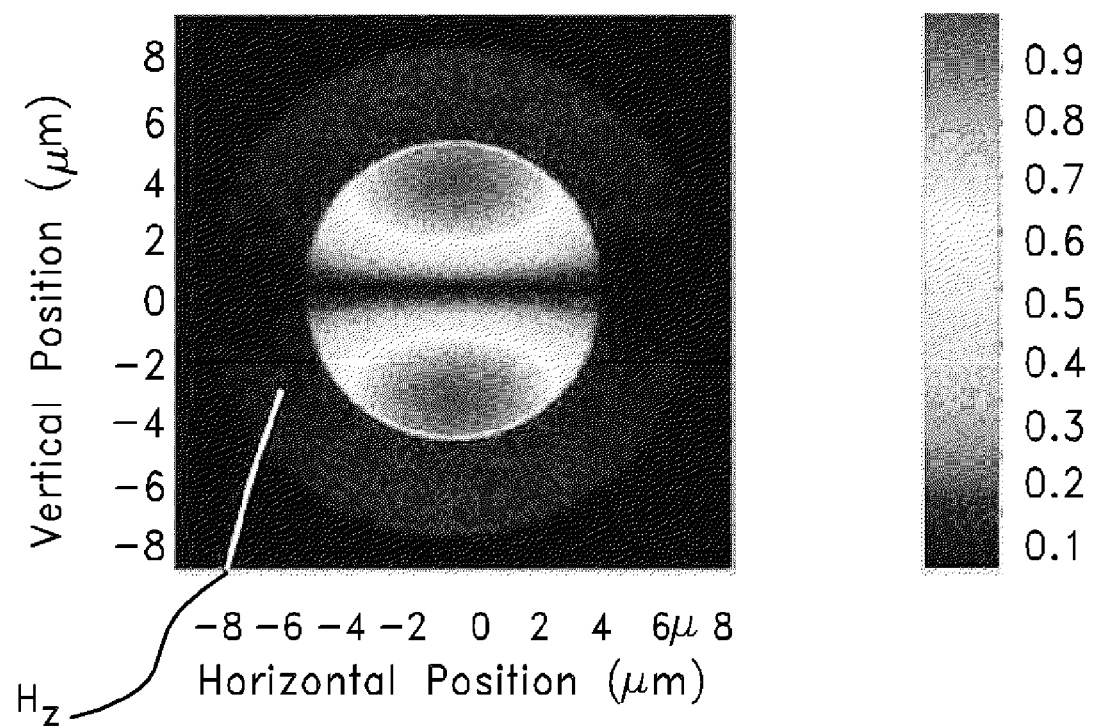
Figure 7A2

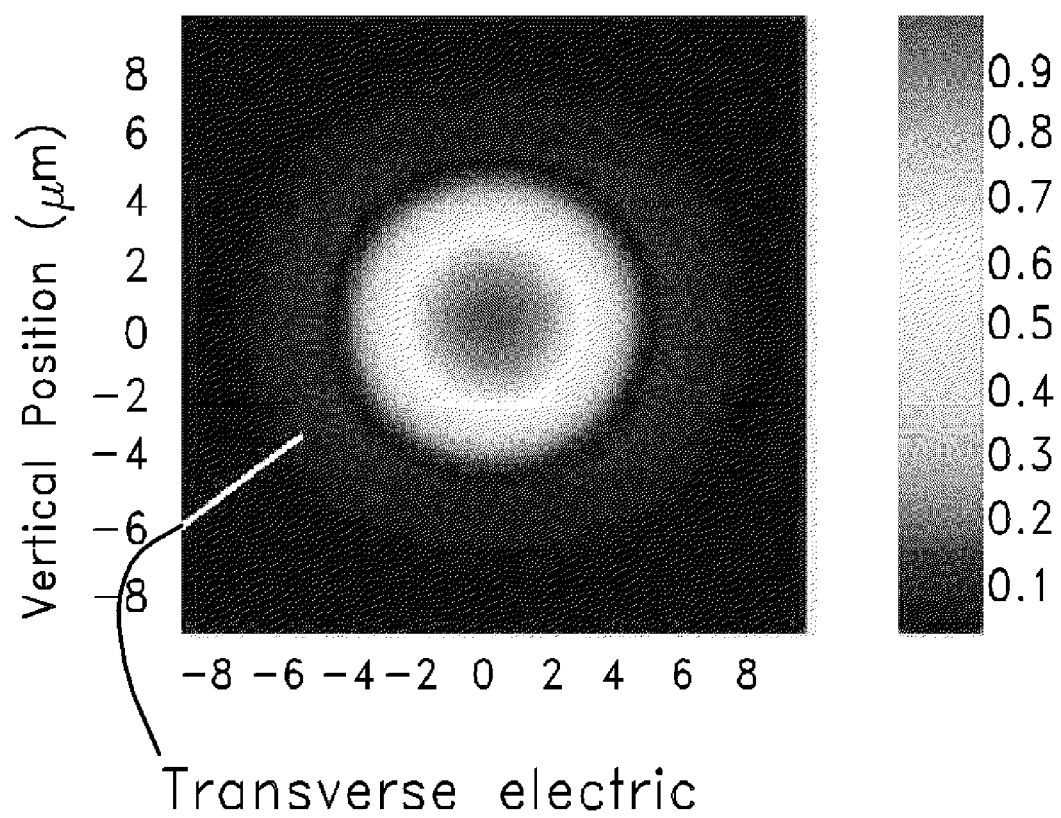
Figure 7A3

PHOTONIC BANDGAP FIBERS

PRIORITY APPLICATION

This application is a divisional of co-pending U.S. patent application Ser. No. 11/686,810, entitled "Photonic Bandgap Fibers" filed Mar. 15, 2007, which is a divisional of U.S. patent application Ser. No. 11/323,177 entitled "Photonic Bandgap Fibers" filed Dec. 30, 2005 (now U.S. Pat. No. 7,209,619) which claims priority to U.S. Provisional Patent Application No. 60/640,345 entitled "Dispersion Control in Photonic Bandgap Fibers" filed Dec. 30, 2004. Each of these applications is incorporated by reference.

BACKGROUND

1. Field of the Invention

This invention relates to optical fibers and more particularly to photonic bandgap fibers.

2. Description of the Related Art

The concept of optical waveguides based on photonic bandgap (PBG) in periodic optical media was first proposed in a theoretical paper by Yeh and Yariv in 1978 ("Theory of Bragg Fibers", Journal of Optical Society of America, vol. 68, no. 9, September 1978, pp. 1196-1201). Not until 21 years thereafter was the first practical demonstration of an optical fiber guided by the PBG effect reported in a paper by Cregan et al published in Science in September 1999 (R. F. Cregan, B. J. Mangan, J. C. Knight, T. A. Birks, P. St. J. Russell, P. J. Roberts, and D. C. Allan: "Single-mode Photonic Bandgap Guidance of Light in Air", Science, vol. 285, September 1999, pp. 1537-1539). In these first demonstrations, the cladding of the optical fiber was formed by triangular stacking of silica capillaries and the core was formed by a central large air hole. The cladding of this fiber was not, in cross-section, a set of concentric circles of different mediums as proposed in the original 1978 paper by Yeh and Yariv, which is referred to as Bragg fiber. The same principles, however, form the basis of both waveguides. A first Bragg fiber demonstration was reported in November 1999 by Fink in a paper published in Journal of Lightwaves Technology (Y. Fink, D. J. Ripin, S. Fan, C. Chen, J. D. Joannopoulos, and E. L. Thomas: "Guiding Optical Light in Air Using an All-Dielectric Structure", Journal of Lightwaves Technology, vol. 17, no. 11, November 1999, pp. 2039-2041).

Since the first demonstration of the photonic bandgap fibers (PBGF) in 1999, progress has been swift. Smith et al reported PBGF with loss as low as 13 dB/km in a paper published in Nature in August 2003 (C. M. Smith, N. Venkataraman, M. T. Gallagher, D. Muller, J. A. West, N. F. Borrelli, D. C. Allan, and K. W. Koch: "Low-loss Hollow-core Silica/air Photonic bandgap Fiber", Nature, vol. 424, August 2004, pp. 657-659). A further breakthrough came in a post-deadline paper at the Optical Fiber Communications Conference in February 2004 (B. J. Mangan, L. Farr, A. Langford, P. J. Roberts, D. P. Williams, F. Couny, M. Lawman, M. Mason, S. Coupland, R. Flea, and H. Sabert: "Low Loss (1.7 dB/km) Hollow Core Photonic Bandgap Fiber", PDP24, Optical Communications Conference, February 2004). Mangan et al reported a PBGF with loss as low as 1.7 dB/km.

This progress has brought the technology closer to real world applications. A first area of application is high energy optical pulse propagation. In general, most of the optical power propagating along the optical fiber is in the core, which typically comprises a hole in the center of the PBGF. Light can effectively propagate in vacuum, air, or inert gas with much lower nonlinear coefficients than solids. Accordingly, such hollow cores are an ideal media to propagate optical pulses with high peak power. Such pulses may not otherwise be guided over substantial distances in a conventional optical fiber due to pulse distortion and/or energy loss from nonlinear processes in the core glass. A first demonstration of such high peak power pulse propagation was reported in a paper in Science published in 2003 by Ouzounov et al (D. G. Ouzounov, F. R. Ahmad, A. L. Gaeta, D. Muller, N. Venkataraman, M. Gallagher, C. M. Smith, and K. W. Koch, Science, vol. 301, 2003, pp. 1702). Xenon gas was used to fill the core during one of the reported experiments. Distortion-free transmission over 100 m with pulse intensities up to $10^{13}$ W/cm$^2$ was achieved.

Accurate dispersion control is useful for optical fibers employed for long haul transmission and pulse shaping. In the absence of nonlinearity, dispersion dictates the pulse evolution during transmission through the optical fiber. In cases where the pulse shape is to be preserved, e.g. in telecommunications and delivery of optical pulses, low dispersion may be desirable. In particular, a flat low dispersion over a wide bandwidth can be helpful. A notable example is wavelength-division-multiplexing in telecommunication where a constant low dispersion level over the wavelength can help provide a uniform performance for all carrier wavelengths. Conversely, in cases where a pre-determined level of pulse shaping is desirable, a high level of dispersion with controllable amount of variation over wavelength may be preferred instead. A notable example is pulse compression in a high energy pulse system, where a combination of second and third order dispersion ($\beta_2$ and $\beta_3$, where $\beta m = d^m \beta / d\omega^m$, and, $\beta$ and $\omega$ are propagation constant and optical frequency) can be used to achieve a fair amount of compensation.

What is needed therefore is the ability to design optical fibers having the desired dispersion characteristics.

SUMMARY

Included among the many structures described herein are photonic bandgap fibers designed to provide a desired dispersion spectrum. Additionally, designs for achieving wide transmission bands and lower transmission loss are also discussed.

As described below, for example, dispersion in a PBGF can be tailored for specific applications by appropriately designing the layers of the cladding. In some case, for example, the strong interaction of core mode with the innermost layer or layers of the cladding can be used to obtain a range of desirable dispersion spectra in PBGFs. For instance, in some fiber designs, smaller dimensions of high index material in the cladding and large core size provide small flat dispersion over a wide spectral range. Additionally, low index cladding features distributed along concentric rings or circles may be used for achieving wide bandgaps. A wide variety of other designs are also possible.

Techniques for the fabrication of PBGF are also described herein. An example fabrication technique includes forming of a preform, which is a large version of the PBGF that may be scaled up, e.g., by a factor of few tens to few hundreds, and drawing of the preform to reduce it to the required fiber diameter, typically few tens to few hundreds of micrometers. Other methods are described.

A variety of applications of photonic bandgap fibers is also presented. Other applications not discussed herein are possible as well.

One embodiment of the invention, for example, comprises a photonic bandgap fiber for propagating light having a wavelength, $\lambda$, comprising a core and a cladding disposed about the core. The cladding comprises a first plurality of ring-shaped regions defined by high index material having an index of refraction, $n_h$, and a second plurality of ring-shaped regions having a low index of refraction, $n_l$. The first plurality of high index ring-shaped regions has an average thickness, d, and an average periodicity, $\Lambda$, such that the ratio $d/\Lambda$ is less than about 0.3. The cladding has a normalized frequency $v=2\pi d(n_h^2-n_l^2)^{1/2}/\lambda$ that is less than about $\pi$ radians and the core has a wavelength transmission band larger than about 100 nm.

Another embodiment of the invention also comprises a photonic bandgap fiber for propagating light having a wavelength, $\lambda$, comprising a core and a cladding disposed about the core. The cladding comprises a first plurality of ring-shaped regions defined by high index material having an index of refraction, $n_h$, and a second plurality of ring-shaped regions having a low index of refraction, $n_l$. The first plurality of high index ring-shaped regions having an average thickness, d. The high index ring-shaped region closest to the core forms a core cladding boundary that has an average thickness, $\delta$, so as to provide a normalized frequency $v=2\pi\delta(n_h^2-n_l^2)^{1/2}/\lambda$ that is less than about 1 radian.

Another embodiment of the invention comprises a photonic bandgap fiber having a transmission band comprising a core larger than about 10 µm and a cladding disposed about the core. The cladding comprises a first plurality of ring-shaped regions defined by high index material having an index of refraction, $n_h$, and a second plurality of ring-shaped regions having a low index of refraction, $n_l$. The first plurality of high index ring-shaped regions has an average thickness, d, and an average periodicity, $\Lambda$, such that the ratio $d/\Lambda$ is less than about 0.2. The fiber has a dispersion between about −50 to 50 ps/nm/km over at least about 100 nm of the transmission band.

Another embodiment of the invention also comprises a photonic bandgap fiber having a transmission band comprising a core and a cladding disposed about the core. The cladding comprising a first plurality of ring-shaped regions defined by high index material having an index of refraction, $n_h$, and a second plurality of ring-shaped regions having a low index of refraction, $n_l$. The first plurality of high index ring-shaped regions has an average thickness, d, and an average periodicity, $\Lambda$, such that the ratio $d/\Lambda$ is less than about 0.2. The high index ring-shaped region closest to the core has a thickness, $\delta$, larger than about 1.1 times the average thickness, d. The fiber has a dispersion below about −50 ps/nm/km over at least about 20 nm of the transmission band.

Another embodiment of the invention comprises a photonic bandgap fiber for propagating light having a wavelength, $\lambda$, comprising a core and a cladding disposed about the core. The cladding comprises a first plurality of ring-shaped regions defined by high index material having an index of refraction, $n_h$, and a second plurality of ring-shaped regions having a low index of refraction, $n_l$. The high index ring-shaped region has an average thickness, d, such that the fiber has a transmission loss of less than about 100 dB/km at a wavelength corresponding to a normalized frequency $v=2\pi d(n_h^2-n_l^2)^{1/2}/\lambda$ between about (a) $0.55\pi$ to $0.85\pi$ (b) $1.05\pi$ to $1.75\pi$, or (c) $2.4\pi$ to $2.7\pi$.

Another embodiment of the invention comprises a photonic bandgap fiber having a transmission band comprising a core and a cladding disposed about the core. The core comprises a first plurality of ring-shaped regions defined by high index material having an index of refraction, $n_h$, and a second plurality of ring-shaped regions having a low index of refraction, $n_l$. The first plurality of high index ring-shaped regions has an average thickness, d, wherein the high index ring-shaped region closest to the core has a thickness, $\delta$, between about 0.1 to 5 times the maximum thickness, d, such that the fiber has zero dispersion at a tailored wavelength.

Another embodiment of the invention comprises an gas analyzer comprising a light source, an optical fiber, and at least one optical detector. The optical fiber comprises a core and a cladding and is optically coupled to the light source. The optical fiber further comprises one or more holes in the core or in proximity to the core for receiving the gas. The at least one optical detector is disposed to receive light from the core of the fiber that is affected by the gas.

Another embodiment of the invention comprises a method of manufacturing a photonic bandgap fiber. The method comprises arranging a plurality of tubes so as to form a plurality of rings of tubes disposed about a center and excluding at least three rings of tubes from the center to provide an open region. The method further comprises stretching the tubes thereby reducing the size of the rings and the open region.

Other embodiments of the invention are also possible.

BRIEF DESCRIPTION OF THE DRAWINGS

FIGS. 2A-2F are cross-sectional views that schematically illustrate PBGF designs having cladding formed from hexagonally arranged microstructures that achieve wider transmission bandwidth and low transmission loss.

FIG. 3A schematically illustrates a Bragg fiber formed from a plurality of larger concentric tubes having varying diameters and a plurality of smaller tubes used to separate larger concentric tubes.

FIGS. 7A and 7B schematically illustrate a HE11 mode resulting from simulations of a Bragg fiber such as shown in FIG. 6.

DETAILED DESCRIPTION OF CERTAIN PREFERRED EMBODIMENTS

Figure 1A:
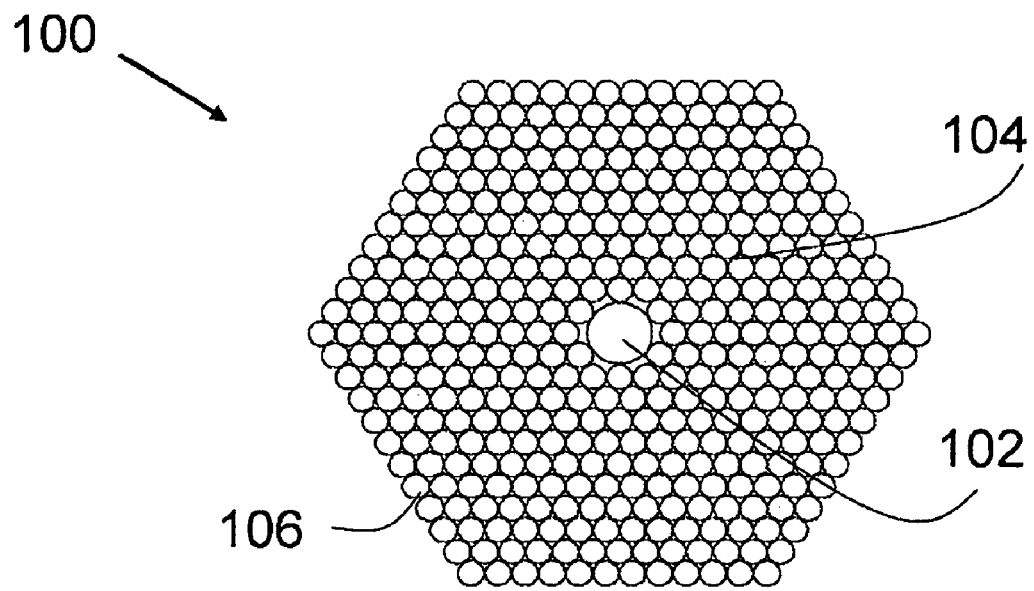
FIGS. 1A and 1B are cross-sectional views that schematically illustrate examples of the photonicband gap fibers (PBGFs) having a cladding fabricated from a plurality of hollow tubes with 7 and 19 tubes, respectively, removed to form a core.
Figure 1B:
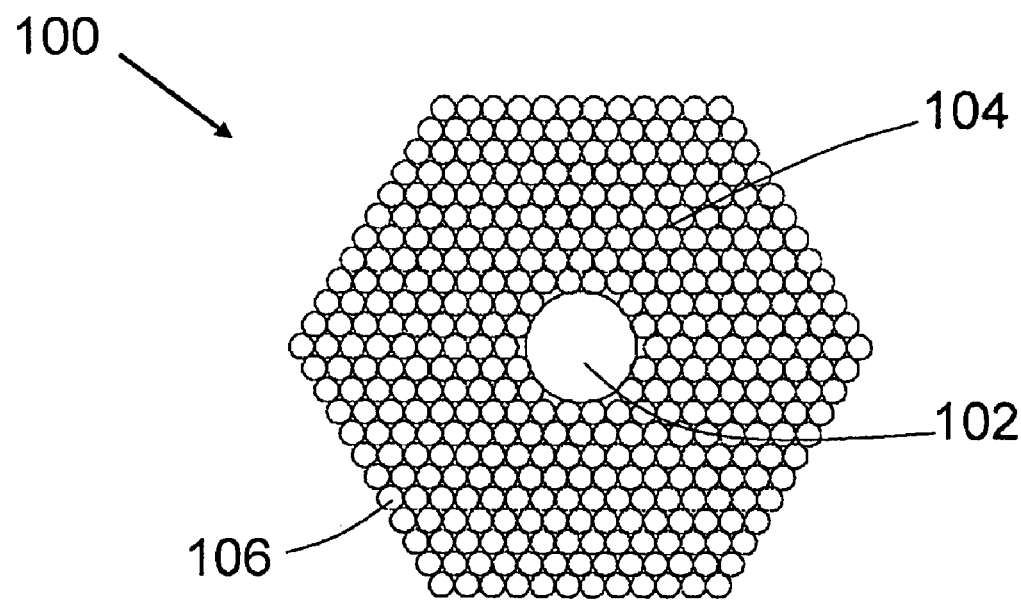

A photonic band gap fiber (PBGF) 100 such as shown in FIG. 1A comprises a core 102 and a cladding 104, wherein the cladding comprising a plurality microstructures 106 arranged along hexagonally-shaped pathways about the core. Such a cladding 104 may, for example, be formed by stacking small thin wall tubes in a triangular pattern. As seen in FIG. 1A, this triangular pattern results in a hexagonal arrangement and may be referred to as hexagonal stacking as well. The core 102 shown in FIG. 1A may be fabricated by excluding 7 tubes from the center of the hexagonally-shaped pathways. In FIG. 1B, the core 102 in the PBGF 100 is formed by leaving out 19 tubes. The fiber in FIG. 1B has a much larger core size.

These fibers may be formed by drawing the tubes. Although the cladding 104 is created by stacking circular tubes, the final cross-section of the fiber 100 typically does not contain circular holes because the interplay of surface tension and viscous flow during the drawing process distorts the circular holes. The holes are typically pressurized during drawing. This pressure plays a major part in determining the final hole geometry.

The tubes may comprises hollow glass tubes, the glass portion comprising a relatively high index material in comparison to the hollow portion, which is empty and may be evacuated or filled with gas or air. After drawing, the glass portions fuse together forming a high index matrix having hollow regions therein. These hollow regions within the glass matrix form the microstructures 106 that provide the photonic band gap confinement of the cladding 104.

These fibers 100 made by removing 7 or 19 tubes from the center of a hexagonal stack, however, have a transmission window of less than 100 nm. Yet for many applications, a much wider transmission band is useful. As described herein, a wider transmission band or window can be achieved by reducing the thickness of the high index materials in the cladding. Additionally, transmission loss has a minimum at an optimized thickness of this high index material in the cladding. Higher leakage loss can result at very small thickness of the high index cladding material, and thus, the cladding no longer provides good confinement. A greater number of tubes or resulting microstructures can be removed from the center to provide for the desired core size. A preform comprising the plurality of tubes with many tubes in the center removed can be drawn down to provide a desired core size. The cladding dimension can be substantially reduced when drawn down to give a desired core size. According, in various embodiments, the transmission band is large, while transmission loss may also be substantially reduced.

Figure 2A:
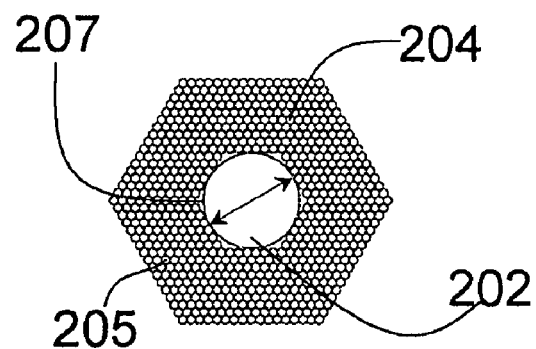

An illustration of the stacked preform is shown in FIG. 2A, comprising a core 202, a cladding 204 formed by stacking tubes 205. A core tube 207 is used to form the core 202. In this method, small dimension for the high index material is achieved by leaving out much more than 19 tubes when forming the core 202 using the triangularly stacked cladding. The preform is then drawn to yield a certain core size after drawing. The cladding dimension is much reduced compared to other designs with a similar core size.

Apart from confinement loss, an additional loss mechanism in PBGF is from the presence of surface modes around the core. Guided core modes can couple power into the surface modes. Part of this coupled power is subsequently lost. The presence of surface modes is a direct consequence of removing tubes in a regular matrix to form a core. Advantageously, however, the number of surface modes can be reduced by reducing or minimizing the width of the high index material around the core. In various preferred embodiments, the width of the core/cladding boundary is much further reduced than that of the corresponding cladding. Much stronger coupling exists between the guided core modes and these surface modes than that of the guided core modes and the modes supported in the cladding. The width reduction of the core/cladding boundary is provided by the techniques described above for reduction the width of the high index material in the cladding structure.

Figure 2B:
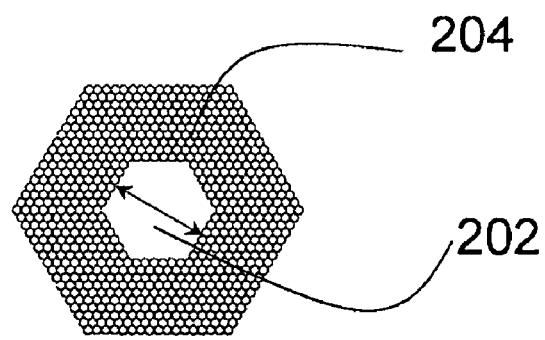
Figure 2C:
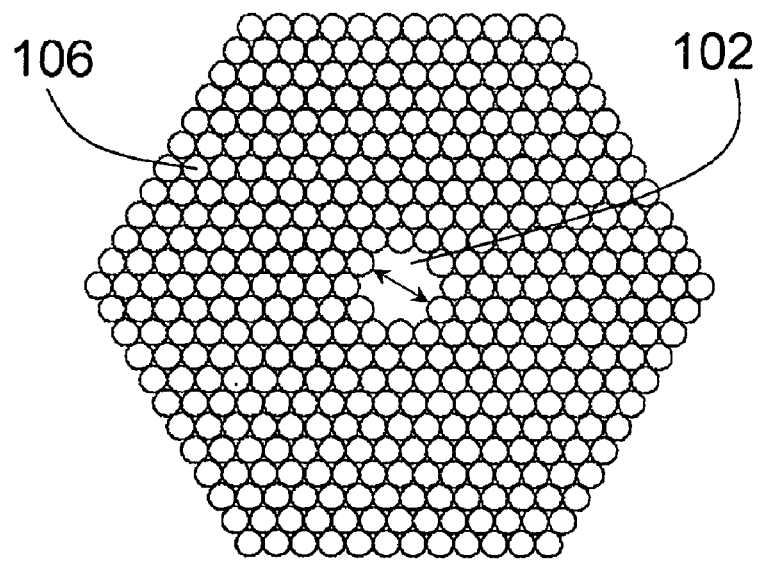
Figure 2D:
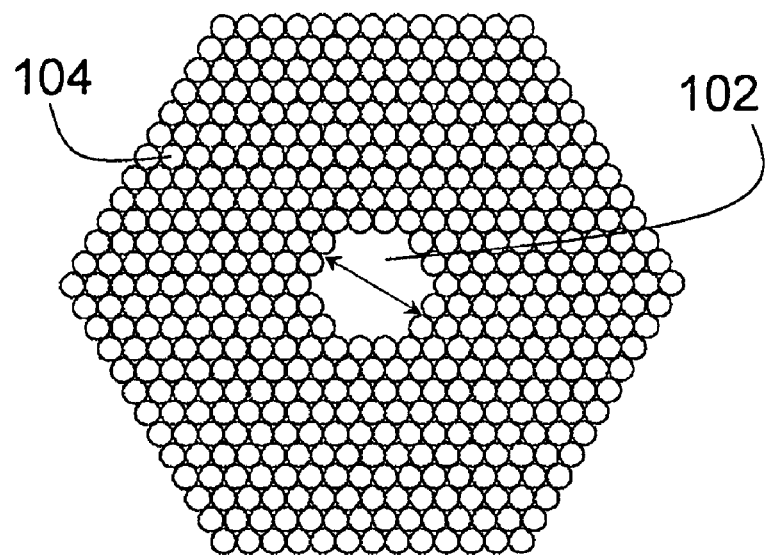

Accordingly, some loss in PBG fibers is due to the presence of surface modes around the core and cladding interface formed by the high index material closest to the core. This high index material may comprises a layer, which may be annular or ring-shaped as seen in the cross-section such as shown in FIG. 2A. This high index material forms a high index boundary around the hollow core 202 that has a relatively low index. The high index material layer may be formed at least in part by the core tube 205. The surface modes are supported by this high index boundary around the core. As described above, these surface modes can act as leakage channels for guided core modes. The core modes can couple power into these surface modes and the power is then lost through further coupling into cladding modes or more likely radiation modes. One method of solving this problem is to reduce the width of the high index boundary around the core. Decreasing the width of the high index boundary may be accomplished by removing the core tube 205 in FIG. 2A. The improved design is schematically illustrated in FIG. 2B, where the core tube 205 is removed to reduce the thickness of the high index boundary around the core 202. The designs in FIGS. 1A and 1B can also benefit from removing the core tubes. These resultant designs are shown in FIGS. 2C and 2D. The core/cladding can also be selectively etched.

Figure 2E:
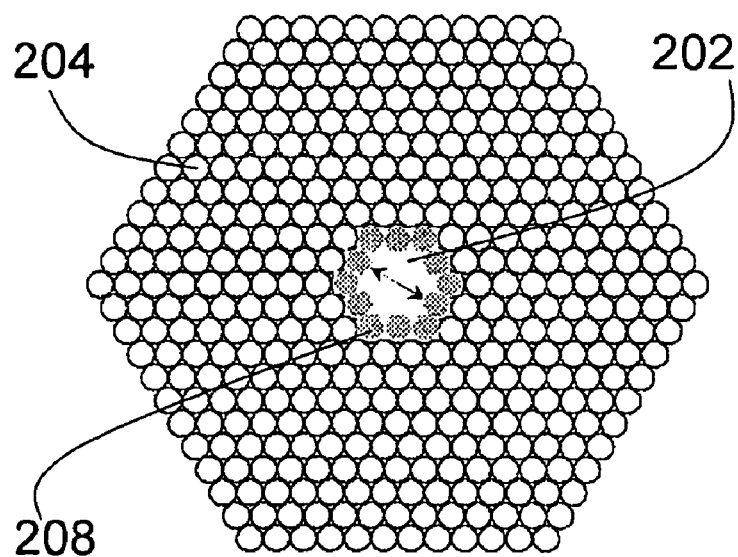

Additionally, a further step can be taken to eliminate surface modes. In this approach, a composite structure 208 is used in place of the tubes closest to the core 204 as is schematically illustrated in FIG. 2E. As shown, each of the tubes around the core are replaced with a composite tube. In this case, for example, twelve composite structures are used. An example of the composite tube or structure 208 is shown in FIG. 2F. This composite structure 208 is formed by stacking tubes 210 and then drawing the tubes down to an appropriate size to incorporate into the final preform. For example, large bundle of stacked tubes forming the composite structure are the drawn down to the same dimension as the tubes in the perform stack.

Repeated stacking and drawing can be used to further reduce the dimension of the high index material. More of the cladding tubes, especially the ones nearer to the core 202, can be replaced by the composite structure 208 to be benefited by the small dimension of the high index material. This approach thus can substantially reduce the glass dimension around the core. The general approach illustrated in FIGS. 2A-2F is not limited to triangularly stacked cladding and can be also be used in other methods of stacking. Other variations are also possible.

As used herein in a consistent manner as used by those skilled in the art, PBG fiber is fiber that guides light therein largely by the photonic bandgap effect. Photonic bandgap effect does not necessarily require a periodic cladding structure and only that there are few guided modes supported the cladding such that the guided modes in the core, which is surrounded or partially surrounded by the cladding, have few pathways to channel power out of the core. The cladding structure in cross-section may comprises a two-dimensional periodic structure formed by a triangularly stacked arrangement of tubes that provides for hexagonally shaped rings of microstructures. The cladding structures may also comprise concentric circular rings of alternative high and low index optical material. In some embodiments, the cladding structures comprise concentric circular rings with holes disposed in alternating ones of these concentric circles. A common features of these cladding designs is the inclusion of at least two optical materials with relatively high and a low refractive indices. To provide various advantages such as described above, in certain preferred embodiments, the physical dimension of the optical material with the high refractive index is small enough so it supports few modes. Typical examples of cladding include cylindrical structures as described by Yeh and Yariv and triangular or hexagonal arrangements of microstructures as described in by Cregan et al. Additional discussion of photonic bandgap fibers is provided in U.S. patent application Ser. No. 10/844,943 entitled "Large Core Holey Fibers" as well as U.S. patent application Ser. No. 11/134,856 entitled "Single Mode Propagation in Fibers and Rods with Large Leakage Channels" are also incorporated herein by reference in their entirety.

As described above, to increase transmission bandwidth and reduce transmission loss of a PBGF, the number of modes supported by the cladding may be reduced, as these supported modes can act as leakage channels to couple out guided modes in the core. An effective way to reduce the number of modes in the cladding is to reduce the width of high index part of the cladding. The high index material in the PBG fibers such as shown in FIGS. 1A and 1B is included in a plurality of ring-shaped regions. In particular, the ring-shaped regions shown in FIGS. 1A and 1B comprise high index material having microstructures formed by openings disposed in the high index material. These ring-shaped regions are arranged about the core. Adjacent ring-shaped regions are also interconnected by webs of the high index material. In a triangularly stacked cladding, these rings take the form of hexagons with increasing size as they are further away from the core. The width of the high index ring-shaped regions in the cladding plays a role in determining the number of modes supported in the cladding, not the area ratio of the high index material and the openings therein having a low refractive index, which is often referred to as air filling factor. As described herein, an optimum width of high index part of the cladding exists that provide for reduced or minimum transmission loss. The details of this optimum width are discussed below using a Bragg fiber as example of a PBG fiber comprising a plurality of concentric ring-shaped regions.

Circular ring-shaped regions offer some performance advantages in comparison to hexagonal ring-shaped regions illustrated in the FIGS. 2C and 2D. These advantages may include wider transmission bandwidth and lower transmission loss. Details are discussed below in connection with results of simulations of Bragg fibers. Such a Bragg fiber comprises the high and low index materials arranged in alternating concentric ring or ring-shaped regions about the core. A Bragg fiber is, however, difficult to implement when using air as the low refractive index material.

FIG. 3A schematically illustrates a Bragg fiber 300 comprising a core 302 surrounded by a cladding 304 comprising substantially circular concentric ring-like regions 306, 308 of high and low index, respectively, wherein the low index region comprises air. The high and low index regions 306, 308 alternate. Note that these regions 306, 308 are circular as seen in the cross-sectional views shown but are cylindrical when considering the longitudinal direction of the fiber 300. In particular, large cylindrical tubes of varying diameters are used to form concentric rings 306. Small tubes are used as spacers 310. The core 302 is disposed at the center of the concentric regions 306, 308.

Figure 3B:
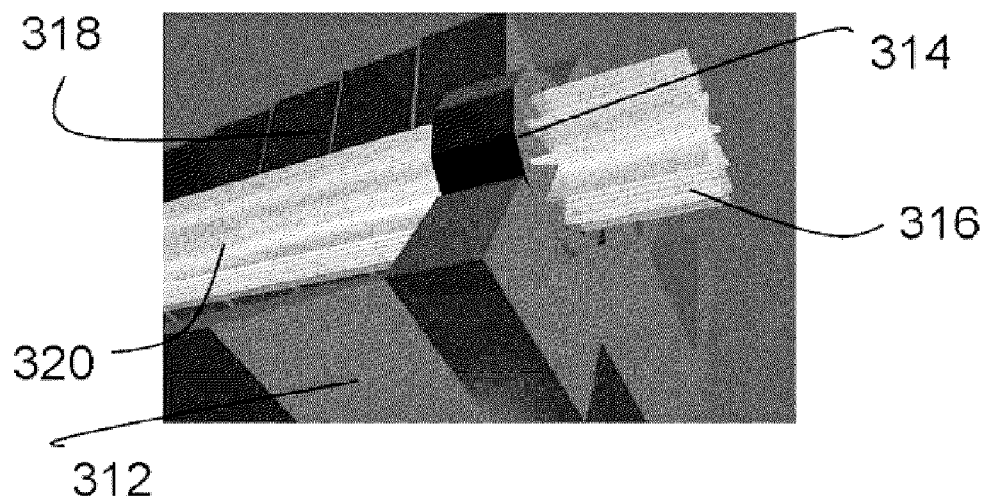
FIGS. 3B-3D schematically illustrates an apparatus and method for fabricating the PBG fiber by stacking circular concentric tubes with varying diameters and introducing the smaller capillaries between the concentric tubes such as shown FIG. 3A.
Figure 3C:
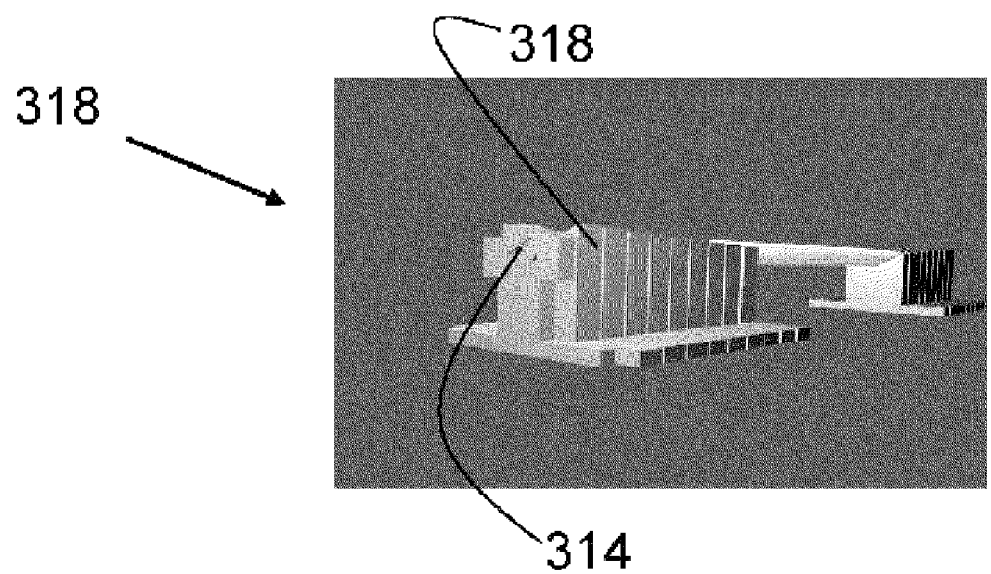
Figure 3D:
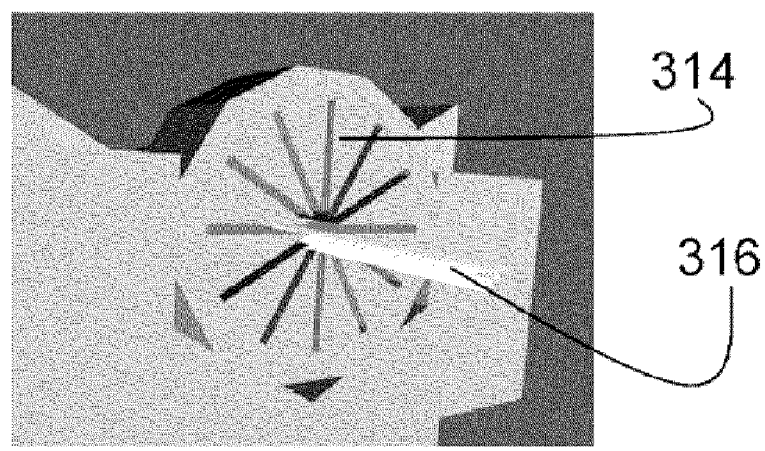

The design in FIG. 3A can be stacked using an apparatus 312 such as illustrated FIG. 3B. The apparatus 312 includes a first holder 314 comprising elongated slots that hold the small tubes 316. A second holder 318 comprises series of V-groves that support the large tubes 320. The apparatus 312 is further illustrated in FIG. 3C, where the elongate slots and V-grooves are shown. The first holder 314 with small tubes 330 is further illustrated in FIG. 3D.

Figure 4A:
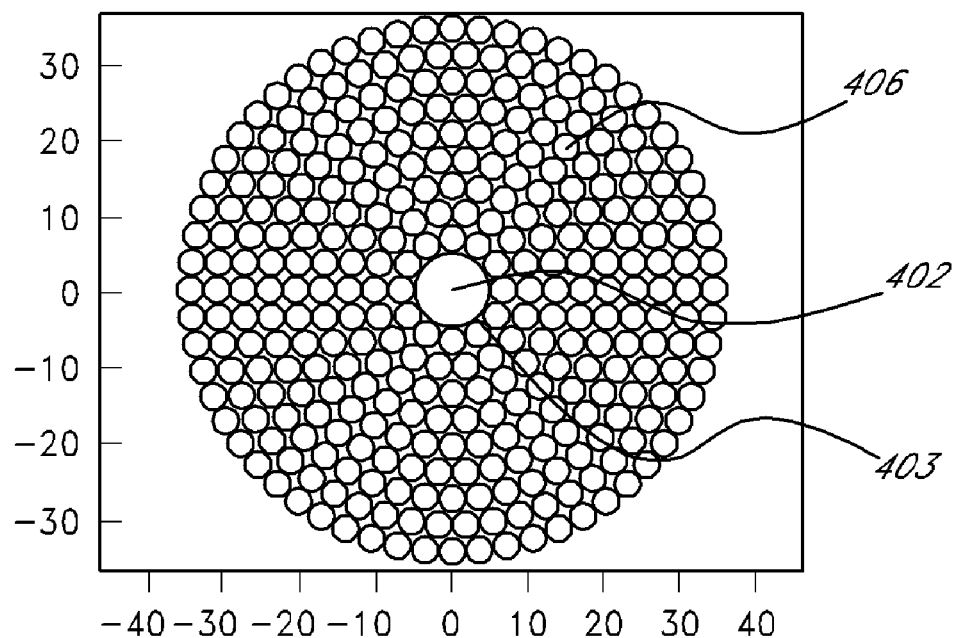
FIGS. 4A and 4B schematically illustrate performs for forming PBG fibers comprising concentric circular rings formed from a plurality of microstructures arranged along concentric circular paths.
Figure 4B:
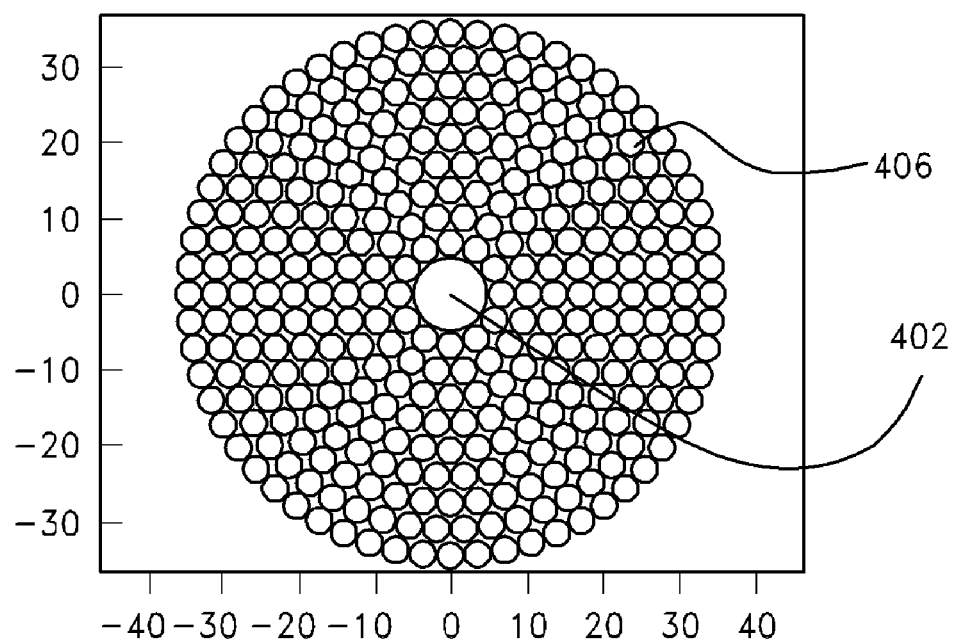

Another design having circular stacking is illustrated in FIG. 4A. A central opening 402 forms the core. A core tube 403 comprising a larger diameter tube is used to form the core/cladding boundary. Small tubes 406 having smaller diameters are used to form the cladding. In the embodiment shown, each of the smaller tubes 406 have the same diameter. The small tubes 406 are arranged in circular patterns. In a preferred embodiment, the core tube 403 is removed as is illustrated in FIG. 4B.

Figure 4C:
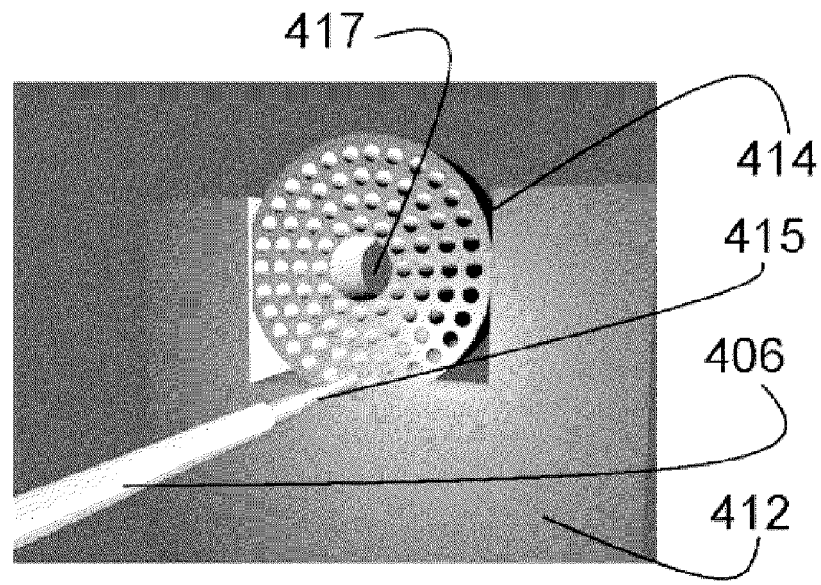
FIGS. 4C and 4D schematically illustrate apparatus and methods for forming the PBG fibers of FIGS. 4A and 4B.
Figure 4D:
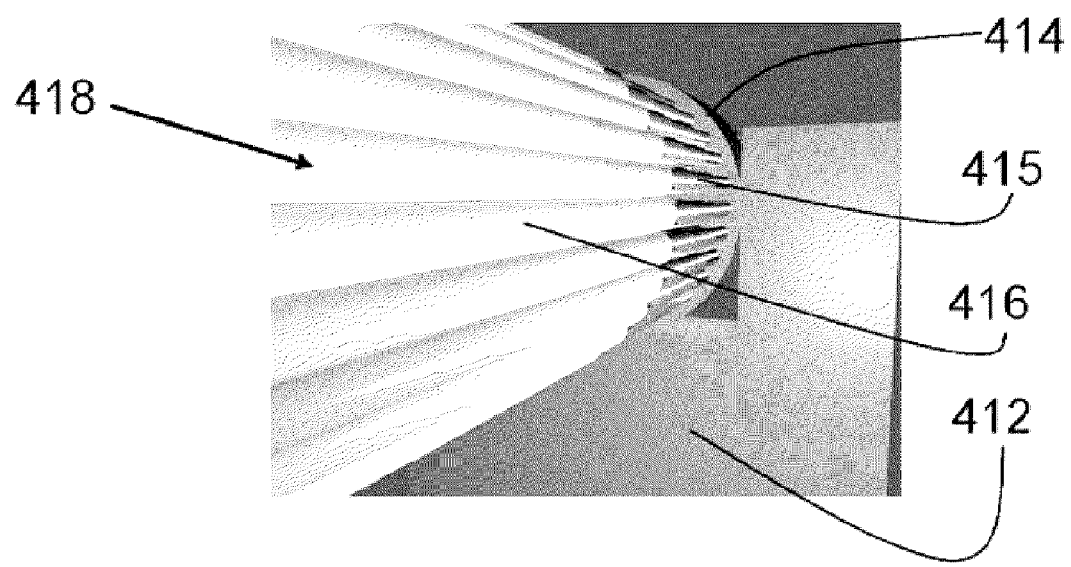

An apparatus 412 used for stacking this preform is shown in FIG. 4C. A holder 414 includes openings that hold pins 415, which in turn hold the small tubes 406. The holder 414 also includes a central opening 417 for holding the core tube 403. A fully stacked preform 418 is further illustrated in FIG. 4D. Although in this example the holder arranged the tubes along concentric circular pathways, the holders can be configured with any arbitrary pattern.

Once a stacked perform is formed, two tapers are made a small distance away from the holders, for example, by heating the tubes at locations in proximity to the holders to fuse the tubes together at the two ends. The holders can then be removed. The stack may be inserted into another larger tube and fused over its entire length with a moving burner. Two ends of the stack may be cut open to allow further etching of surface layers and deposition of high purity softer glass using, e.g., a chemical vapor deposition system. The etching process can help to remove surface contamination. The deposition of a softer glass layer on the surface layers can help to reduce scattering loss by providing a smoother surface. The perform is subsequently drawn to form fiber.

Figure 4E:
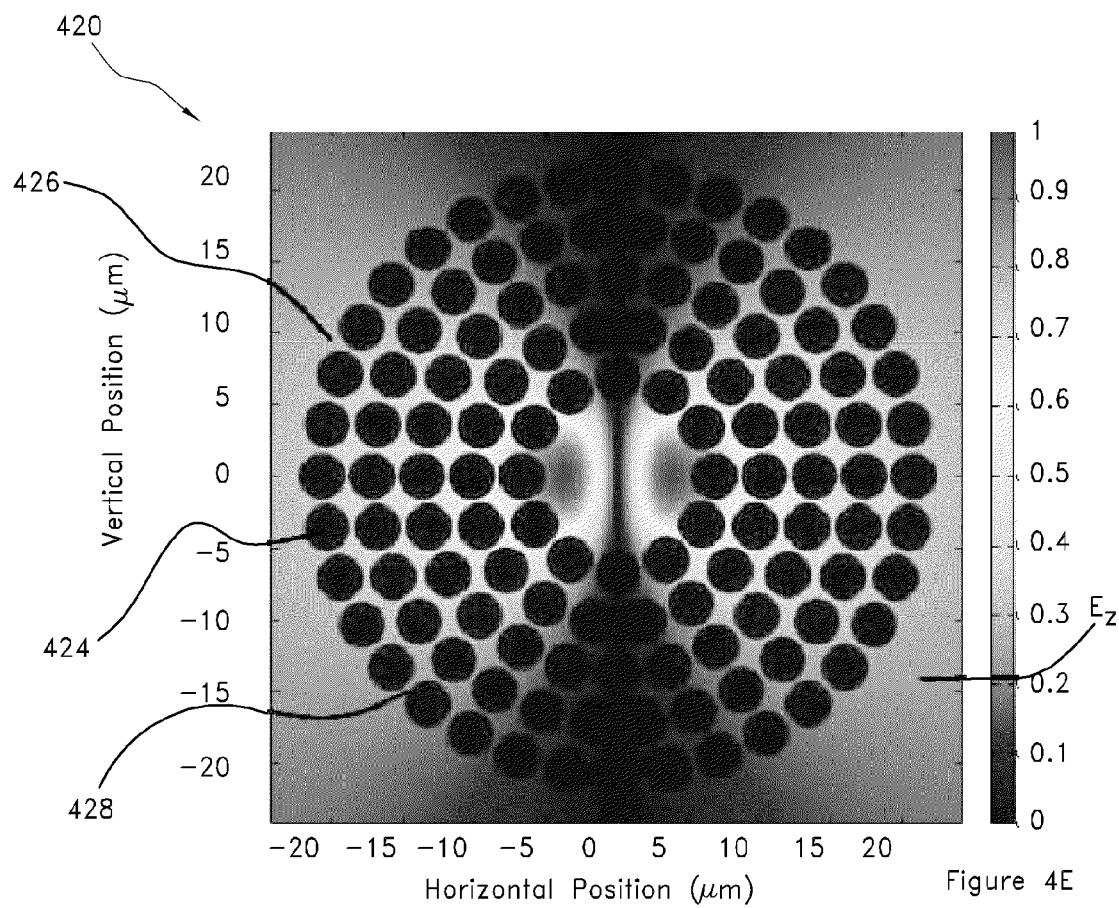
FIGS. 4E-4G schematically illustrate simulated optical modes in the PBG fibers comprising microstructures arranged in concentric circular paths similar to FIGS. 4A and 4B.

Simulations have been performed for a fiber 420 shown in FIG. 4E. As illustrated in FIG. 4E, the fiber 420 comprises a plurality of microstructures 424 arranged in concentric circular patterns. The microstructures 424 comprise holes or openings formed in a matrix material 426. The holes or openings are evacuated or filled with air or gas that yields a relatively low refractive index in comparison to the matrix material 426 which may comprises, e.g., glass, and has a relatively high refractive index. The arrangement of microstructures 424 in the matrix material 426 creates concentric ring-shaped regions of high index material (the glass) and concentric ring-shaped regions of low index (the openings). Adjacent ring-shaped regions are connected by webs 428 of the high index material 426.

Figure 4F:
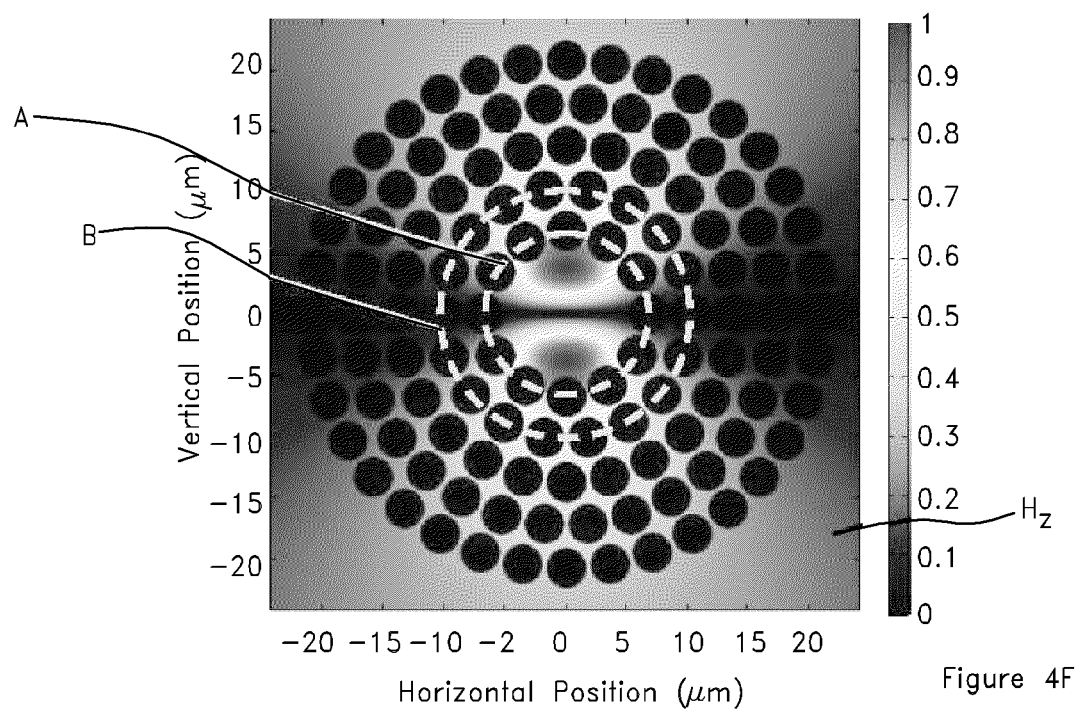
Figure 4G:
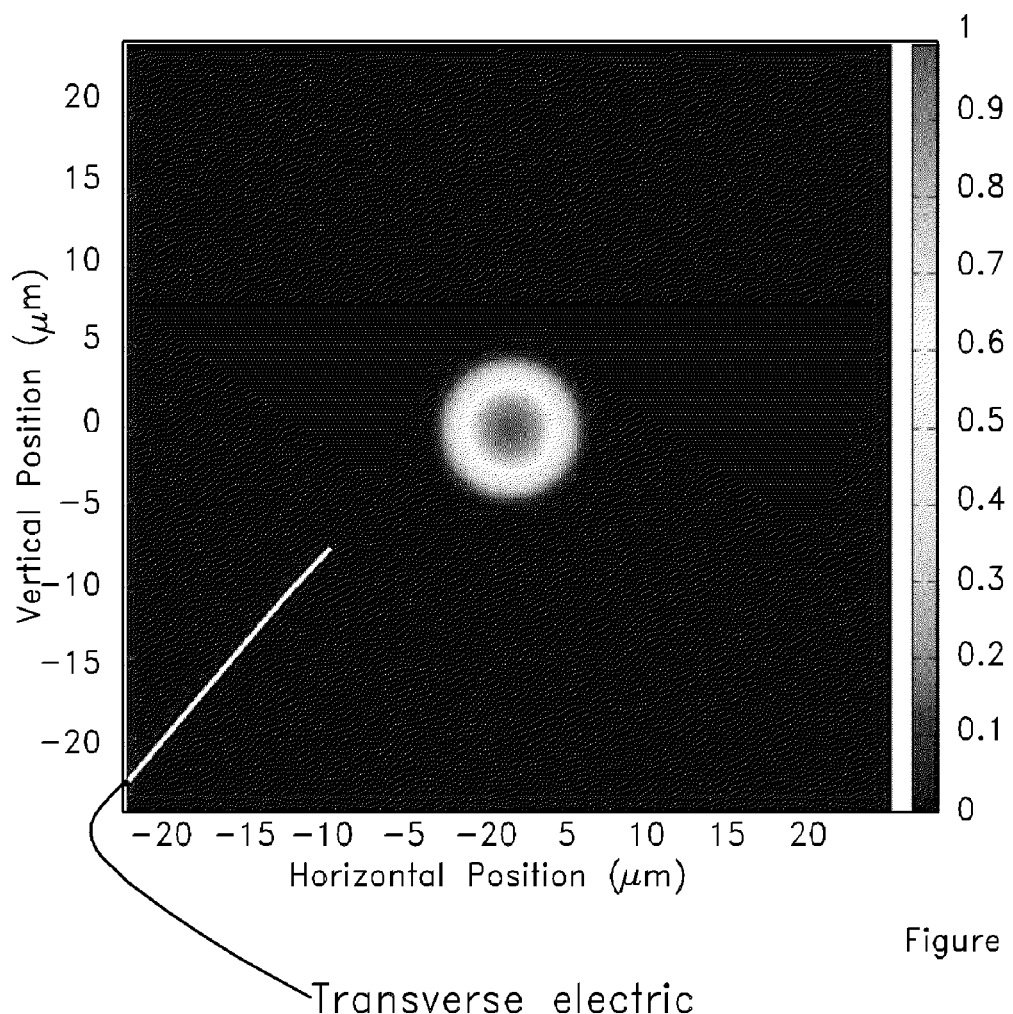

Simulated fields of the HE11 mode are shown in FIGS. 4E-4G. FIG. 4E shows the longitudinal electric field, FIG. 4F shows the longitudinal magnetic field, and FIG. 4G shows the transverse electric field.

Figure 4H:
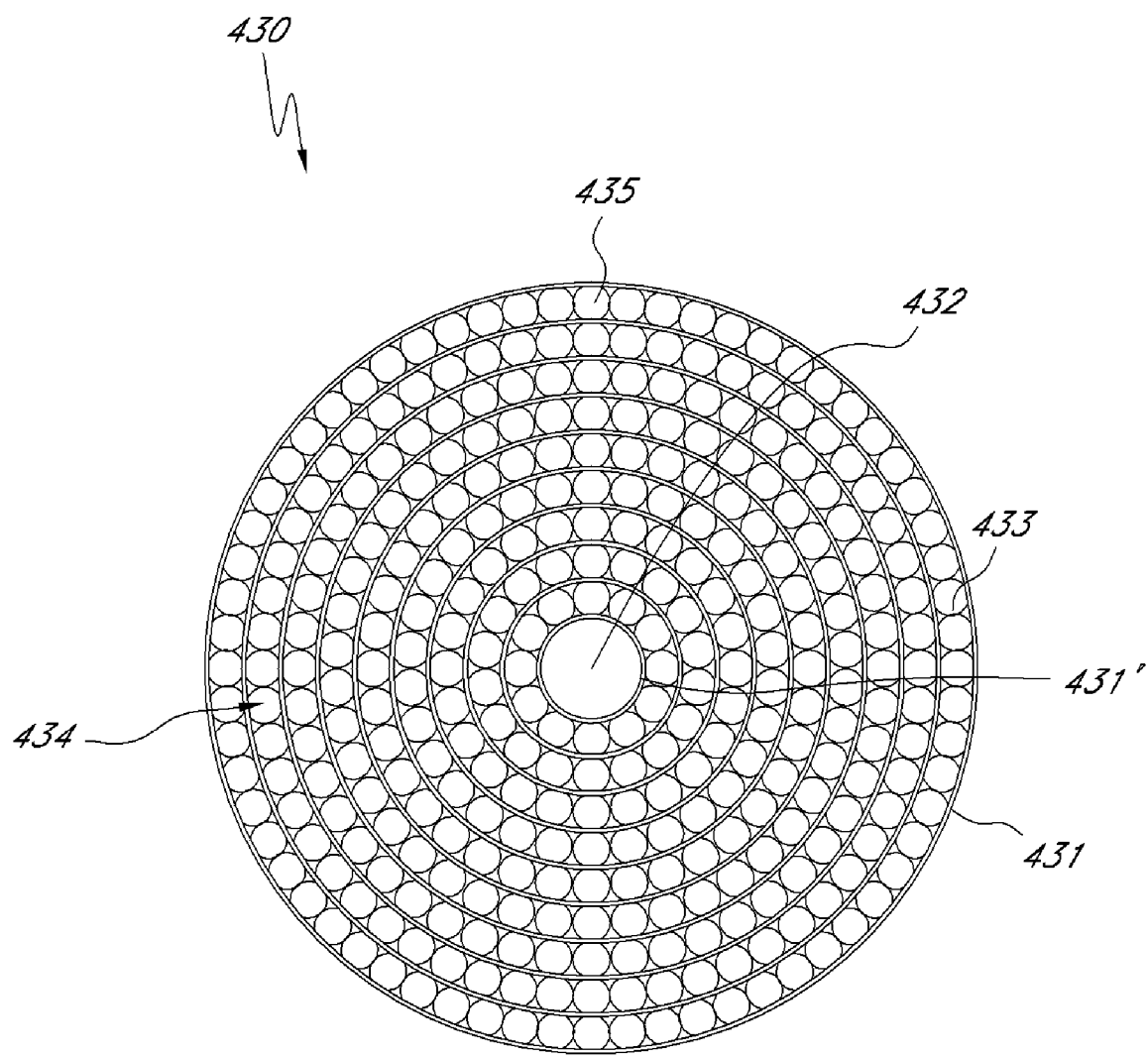
FIG. 4H schematically illustrates first and second pluralities of annular ring-shaped regions of high and low index formed from a plurality of tubes arranged in circular paths fused together.

FIG. 4H illustrates an example of a drawn fiber 430 comprising a core 432 and a cladding 434. The hole boundaries (sidewalls of the small tubes 416) are joined to form a first plurality of concentric rings or ring-shaped regions 431 having circular cross-sections centered at the center of the core 432. These ring-like regions 431 comprise the relatively high index material, e.g., glass. The rings 431 are linked together by webs 433 formed from part of the hole boundaries (e.g., sidewalls of the small tubes 416). These webs 433 comprise the high index material as well. The innermost ring-shaped region 431', the layer closest to the core 432, is also indicated. The fiber 430 also includes a second plurality of concentric rings or ring-shaped regions 435 having circular cross-sections centered at the center of the core 432. The second plurality of ring-shaped regions 435 comprises the circular arrangement of evacuated or gas or air filled openings forming the microstructures and has a relatively low index. The first and second ring-shaped regions 431, 435 alternate.

To assess the affect of the width of the high index material in the core/cladding boundary of a PBGF for reducing or minimizing the number of supported surface modes, simulations are performed. In particular, the mode supported by a high index rod of radius $\delta$ and index $n_h$ embedded in a low index background of index $n_l$ is calculated for a wavelength $\lambda$. In this case, the V value derived for conventional optical fiber can be used.

$$V = \frac{2\pi\delta}{\lambda}\sqrt{n_h^2 - n_l^2} \quad (1)$$

Only a fundamental mode is supported when V<2.405 and this fundamental mode will never cut off. At least 2 modes are supported if the fundamental mode is considered to have a two-fold degeneracy. In practice, the supported mode can, however, be so weakly guided when V is small, that the fundamental mode is effectively not supported. To obtain this practical limit for V, the loss of a bent optical fiber is determined using the loss formula given by Snyder and Love in Optical Waveguide Theory (Chapman and Hall, 1983). If power transmission in an optical fiber can be expressed as $P(z)=P(0)\exp(-\gamma z)$ over a bent fiber having a bend radius of $R_c$, $\gamma$ can be obtained in the following formula for the fundamental mode in a step index fiber.

$$\gamma = \frac{\sqrt{\pi}}{2\delta}\sqrt{\frac{\delta}{R_c}}\frac{U^2}{V^2 W^{3/2} K_1(W)^2}\exp\left\{-\frac{4}{3}\frac{R_c}{\delta}\frac{W_\Delta^3}{V^2}\right\} \quad (2)$$

where U and W are as normally defined for a waveguide, $K_1$ is modified Bessel function of the 1$^{st}$ order, and $\Delta=(n_h-n_l)/n_h$. For small V, where V≈U, the bend loss formula can be simplified.

$$\gamma = \frac{\sqrt{\pi}}{2\delta}\sqrt{\frac{\delta}{R_c}}\frac{1}{W^{3/2} K_1(W)^2}\exp\left\{-\frac{4}{3}\frac{R_c}{\delta}\frac{W^3\Delta}{V^2}\right\} \quad (3)$$

Figure 5:
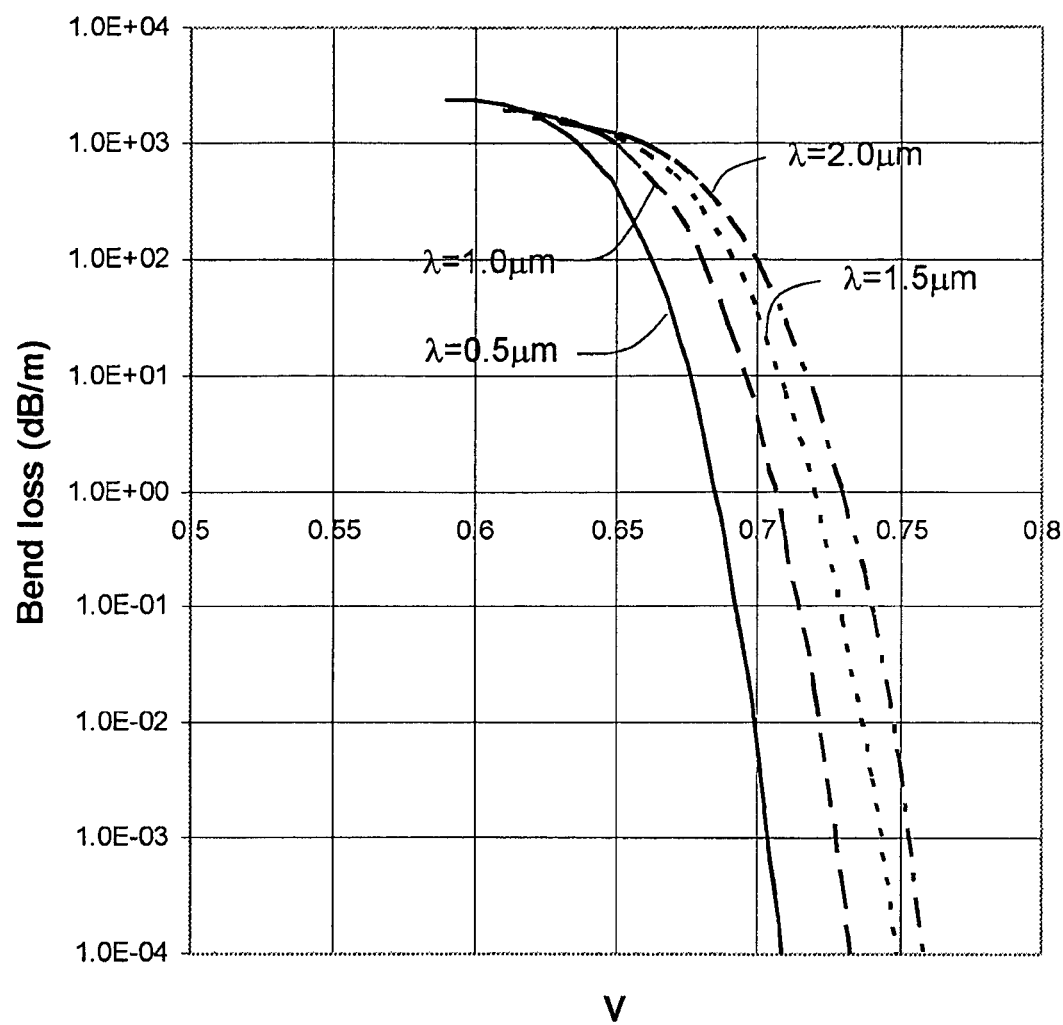
FIG. 5 is a plot that shows bending loss for a 15 cm bending radius for a glass rod having a refractive of 1.45 disposed in air having refractive index of 1.

The bend loss is calculated for a glass rod of refractive index of 1.45 surrounded by air with a refractive index of 1 for a bending radius of 15 cm and shown in FIG. 5. The bending loss is plotted in dB/m for four wavelengths at 0.5, 1.0, 1.5 and 2 μm. The bending loss exceeds 1000 dB/m at around V=0.64-0.66 for all the wavelengths considered. Considering the arbitrariness of the choices of 1000 dB/m and 15 cm bending radius, a V value of 0.5 provides a reasonable practical guidance for fundamental mode cut off. In this example, using the V value of 0.5, the rod diameter is as small as 76 nm, 152 nm, 227 nm and 303 nm for the wavelengths of 0.5 μm, 1.0 μm, 1.5 μm and 2.0 μm. These numbers offer an approximate upper limit for the thickness of the high index material in the core/cladding boundary of PBGF not to support any modes in a practical sense. In this case, $\delta$ is chosen to be the maximum thickness of the high index core/cladding boundary. In practice, it is not necessary to go far below this limit, as less benefit is expected in terms of eliminating surface modes, while benefit of the first layer's contribution to confinement loss will be substantially reduced when $\delta$ is too small. The guided mode will also more likely penetrate through this core/cladding layer if it is too thin. This can increase scattering loss due to imperfections in this layer in addition to the increase of confinement loss. Although, this analysis is done for $n_h$=1.45 and $n_l$=1.0, the same analysis can be done for any other two material combination. In a cladding with layers of high index materials, the maximum thickness of core/cladding boundary layer may need satisfy the above limit. This design approach may be used for triangularly stacked cladding where the high index layers are in the form of hexagons surrounding the core as well as a Bragg fiber. This approach is also applicable to other designs. The range of thickness values, however, is not limiting as values outside these ranges can be used. Other variations are also possible.

Figure 6:
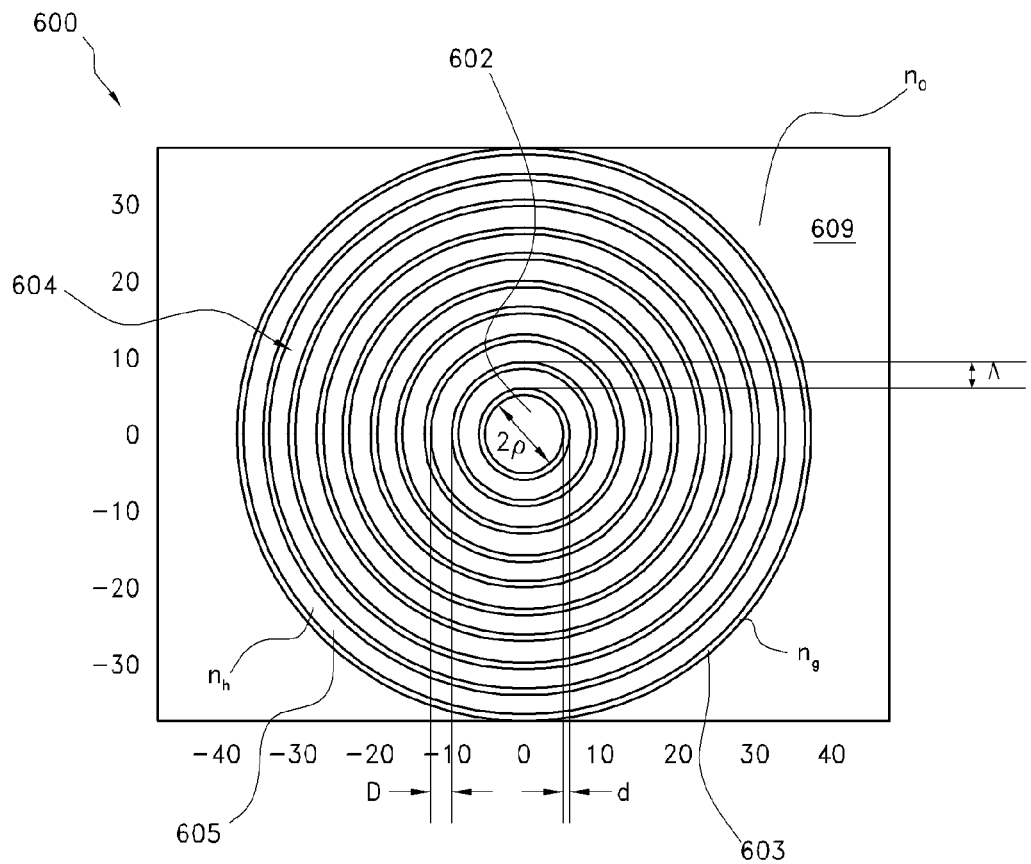
FIG. 6 schematically illustrates a cross-section of a Bragg fiber comprising a plurality of concentric ring-shaped regions of high and low index.
Figure 6:
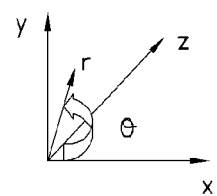

Bragg fiber formed by alternating glass and air layers have been discussed above. The cross-section of a Bragg fiber 600 is shown in FIG. 6. This cross-sectional view shows a core 602 and cladding 604. The cladding 604 comprises a plurality of ring-shaped regions 603, 605 of alternating high and low refractive index. The ring-shaped regions 603 of high index may comprise material having a relatively high index of refraction and the ring-shaped regions 605 of low index may comprise material having a relatively low refractive index.

Certain parameters are also shown in FIG. 6. Λ is the period of periodic cladding. d is the thickness of the high refractive index layers ($n_h$) 603 and D is the thickness of low refractive index layers ($n_l$) 605. The index of the media 609 outside the cladding region 604 is defined as $n_0$. $n_0$ has a small imaginary part in the simulations to enable the calculation of modal confinement loss. N is total number of layers. When a layer has different properties, a subscript n is used to denote each parameter. n is between 1 to N, where 1 denotes the innermost layer. Ratio R is defined as d/Λ. Chirp is defined as $(\Lambda_{i+1}-\Lambda_i)/\Lambda_i$, which remains constant for all layers in the simulation of the Bragg fiber of FIG. 6. The core 602 has a radius of ρ. The following values are used in the simulations if not specifically given: $n_h$=1.45, $n_l$=1, $n_0$=1+i1e−8, ρ=5 μm, R=0.1, Λ=3.5 μm, chirp=0 and number of layer N=10. When a chirp is introduced, $\Lambda_1$=3.5 μm is used, i.e. the first layer was not changed. Despite that the Bragg fiber 600 is used for various simulations discussed herein, the general conclusion should apply to other types of PBGFs.

Figure 7B:
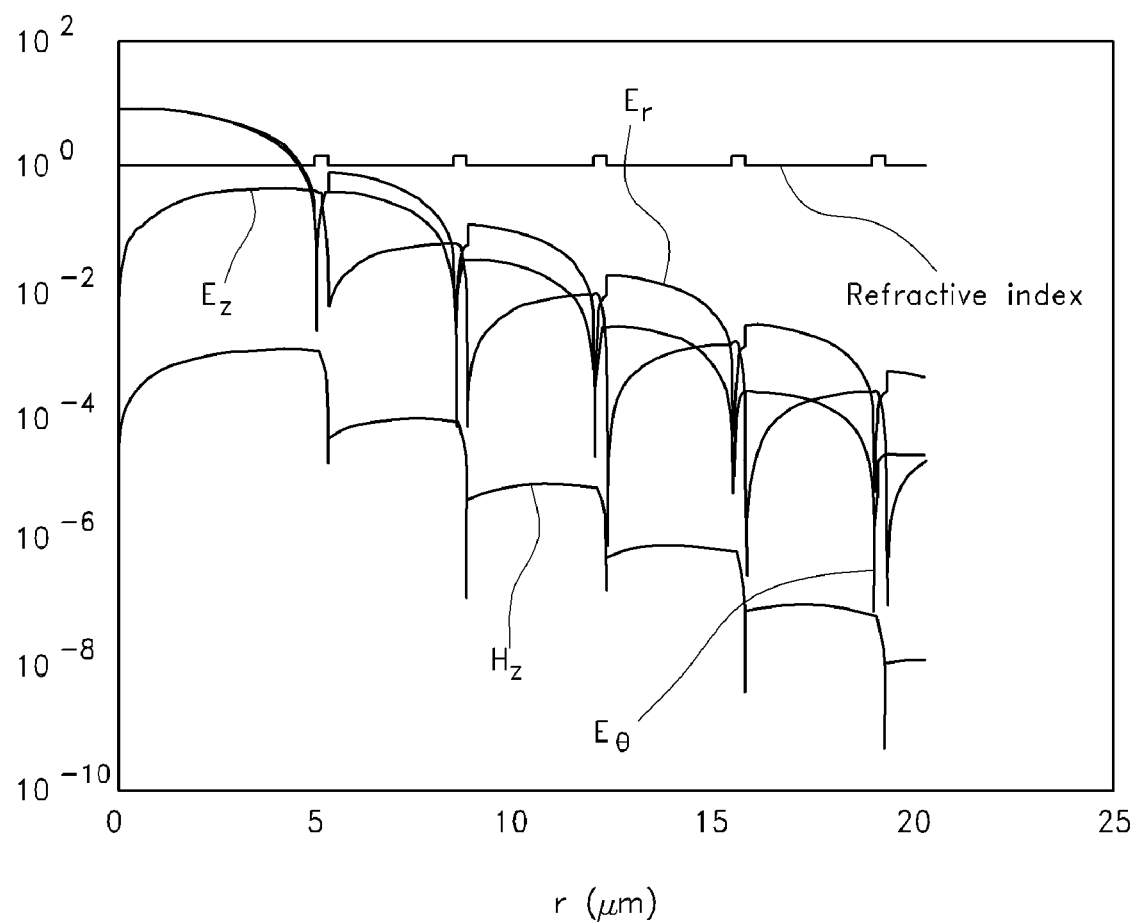

This model is based on boundary field matching with fields decomposed in a Fourier-Bessel series. A simulated HE11 mode in a Bragg fiber is illustrated in FIGS. 7A and 7B. The longitudinal electric field, longitudinal magnetic field and transverse electric field are given in FIG. 7A, while the radial distributions of the $E_z$, $H_z$, $E_r$ and $E_\theta$ are given in FIG. 7B.

Figure 8:
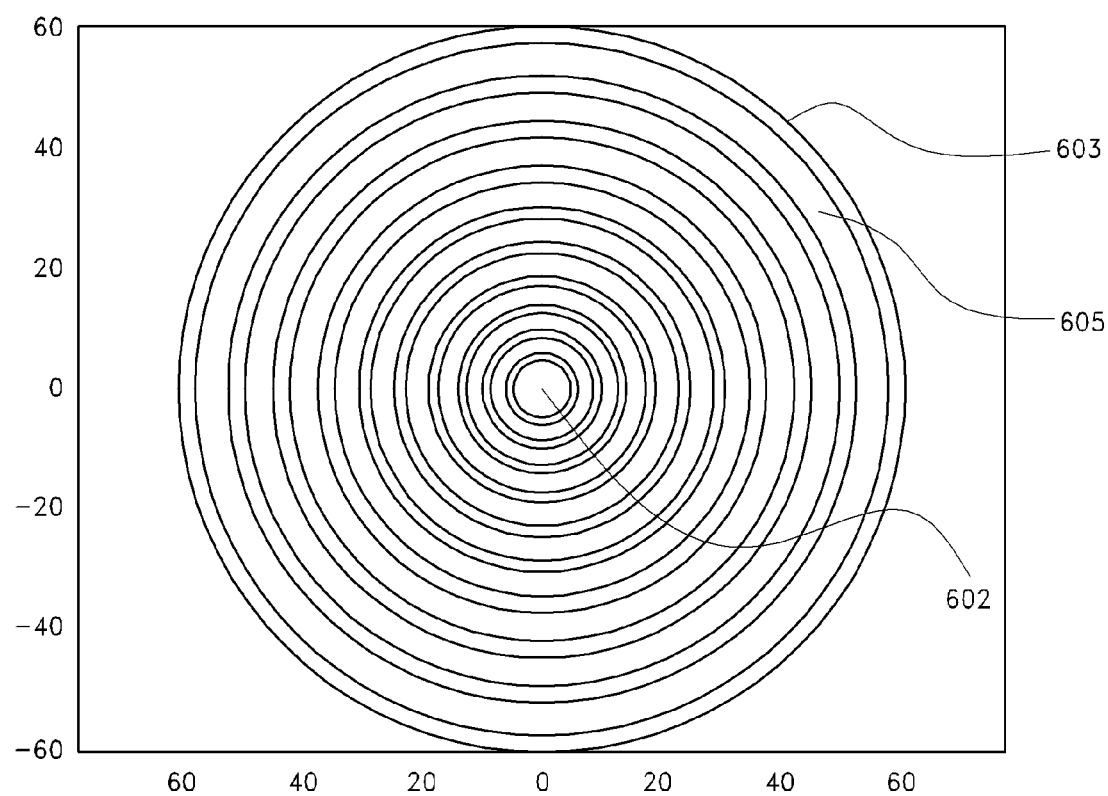
FIG. 8 schematically illustrates cross-section of a chirped Bragg fiber comprising concentric ring-like regions of high and low index having thicknesses that increase with radial distance from the center.

Two types of chirped Bragg fiber are also studied. The first type is illustrated in FIG. 8, where both the period Λ and thickness d of the high index layer 603 are changed from layer to layer in a linear fashion. In a second type of chirped structure, only the period Λ is changed while the thickness d of the high index layer is kept constant (not shown).

Figure 9:
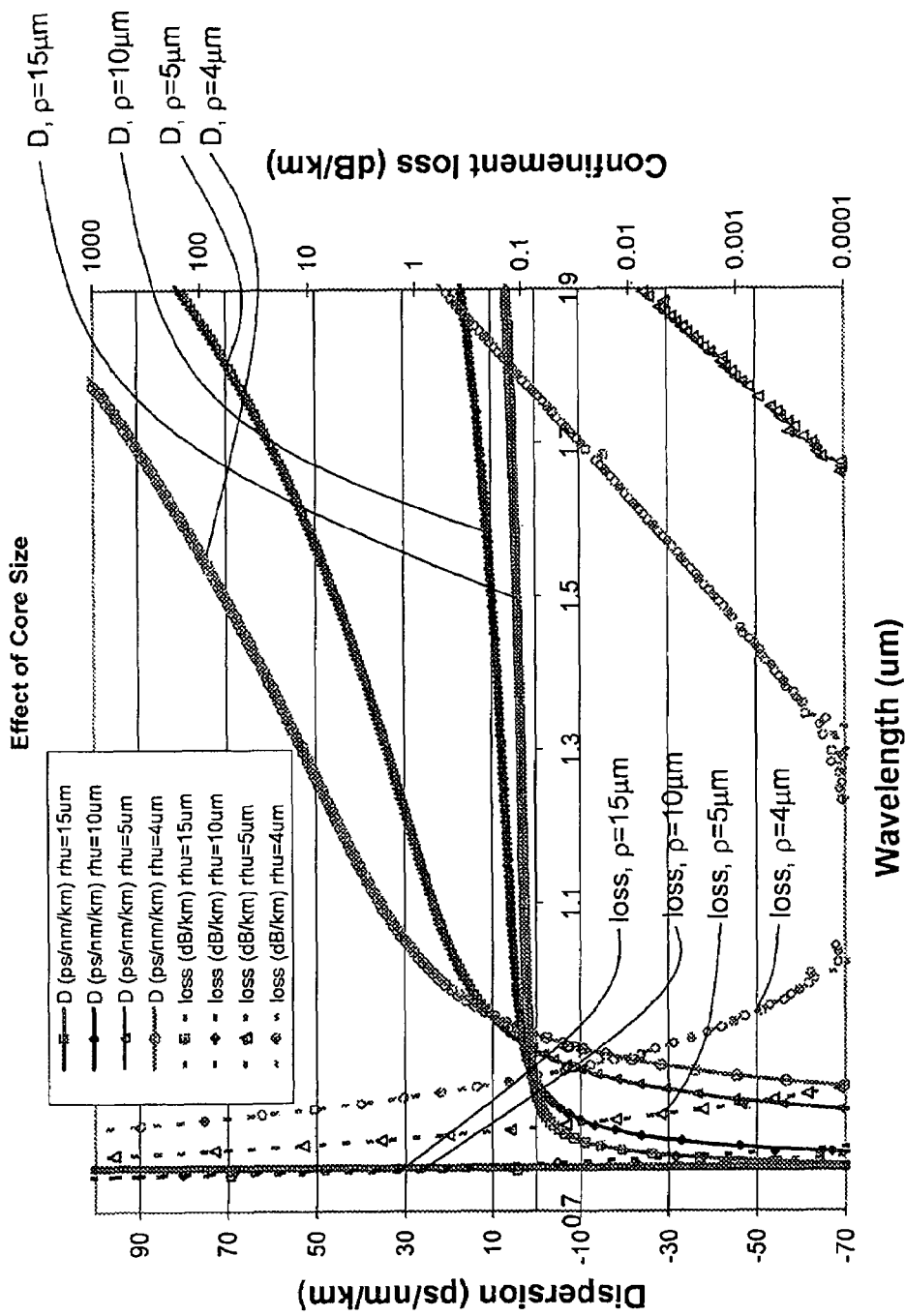
FIG. 9 is a plot of dispersion and confinement loss versus wavelength schematically illustrating the effect of core size in a Bragg fiber.

The effect of core radius on fiber dispersion is shown in FIG. 9. Four core radii, 15 μm, 10 μm, 5 μm, and 4 μm, were studied. Mode confinement loss is shown using dotted lines while dispersion is shown with solid lines. As core size increases, the transmission windows widens and dispersion is generally reduced. A low flat dispersion over a wide spectrum can be achieved at large core size. Such a dispersion characteristic is suitable for telecommunication where multiple wavelengths are transmitted over a wide wavelength range. The ratio (d/Λ) in this simulation is 0.1.

Figure 10:
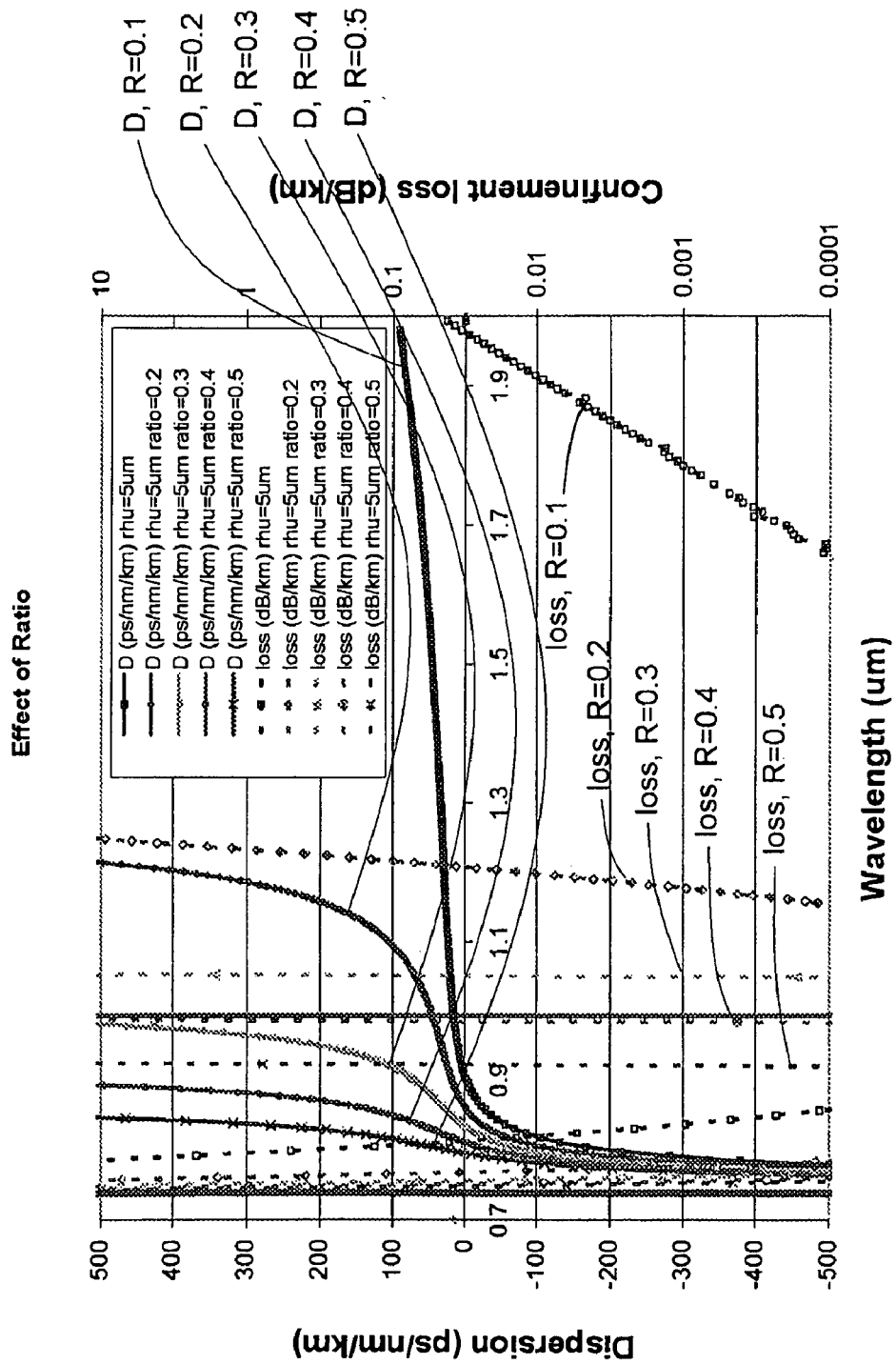
FIG. 10 is a plot of dispersion and confinement loss versus wavelength schematically illustrating the effect of ratio the average thickness and period (d/Λ) of the high index region determined by simulating a Bragg fiber.

Effect of ratio, R=d/Λ, is shown in FIG. 10, where five ratios, 0.1, 0.2, 0.3, 0.4 and 0.5 were simulated. The most significant effect of an increasing ratio, R, is narrowing of transmission window. This effect is accompanied by a strong increase of dispersion, while the dispersion slope is also significantly increased. For a low flat dispersion over a wide spectrum range as desired in a telecommunications system, small ratio may therefore be useful. Moreover, by employing a combination of small ratio and large core, a very low flat dispersion profile over a wide spectrum range is possible. The core size in this simulation is 5 μm. As shown in FIG. 9, dispersion between 0 to 7 ps/nm/km over a bandwidth as wide as 1000 nm can be obtained with a ratio of 0.1 and a core size of 15 μm.

Figure 11:
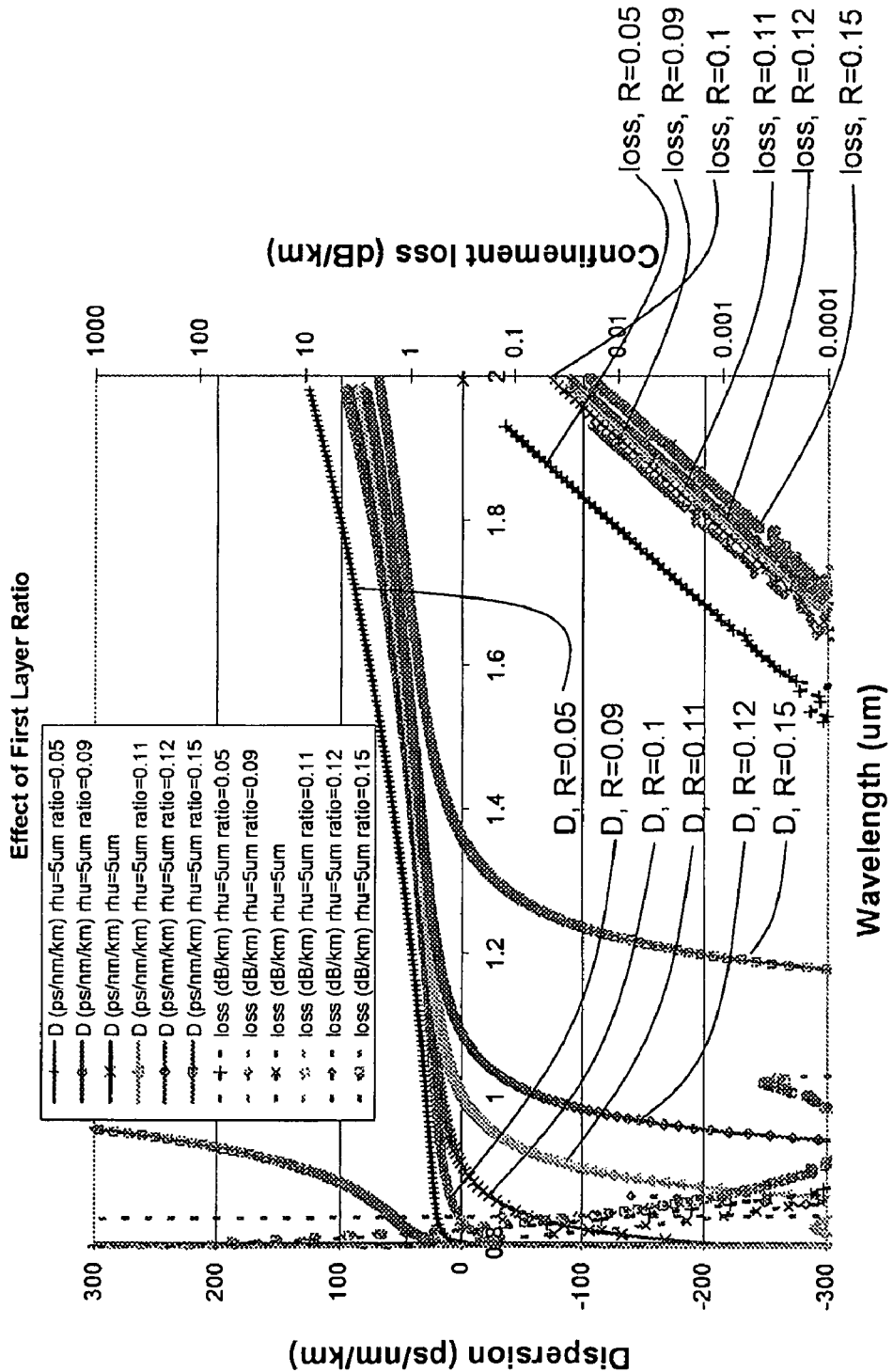
FIG. 11 is a plot of dispersion and confinement loss versus wavelength for a Bragg fiber showing the effect of the ratio of the thickness of the first layer of high index material and the period of the high index layers.

In the plots in FIG. 11, only the ratio, R=d/Λ, of the first layer of high index material 603 was changed. In these simulations, the ratio is determined using the thickness of the first layer 603 as the value for d. As shown, dispersion and zero dispersion wavelength can be modified by adjusting the first layer ratio while the transmission is minimally impacted as long the change of the ratio, R, is not too large. In this example, first layer ratio may be less than 0.15. FIG. 11 demonstrates that the zero-dispersion wavelength can be significantly moved towards the center of the transmission window by increasing the ratio, R=d/Λ, of the first layer 603 (where d is the thickness of this first layer). This result is significant as the high negative dispersion part of the spectrum can thus be used without causing significant transmission loss.

As the curves can be shifted in wavelength by proportionally scaling Λ, any desired part of the dispersion curve can be used by shifting it to a specific wavelength of interest. Dispersion tailoring can be done for any wavelength this manner. Although the effect of the ratio and core size are studied, the refractive index of the first layer 603 can also be similarly adjusted to obtain the desired dispersion in a PBGF.

Figure 12:
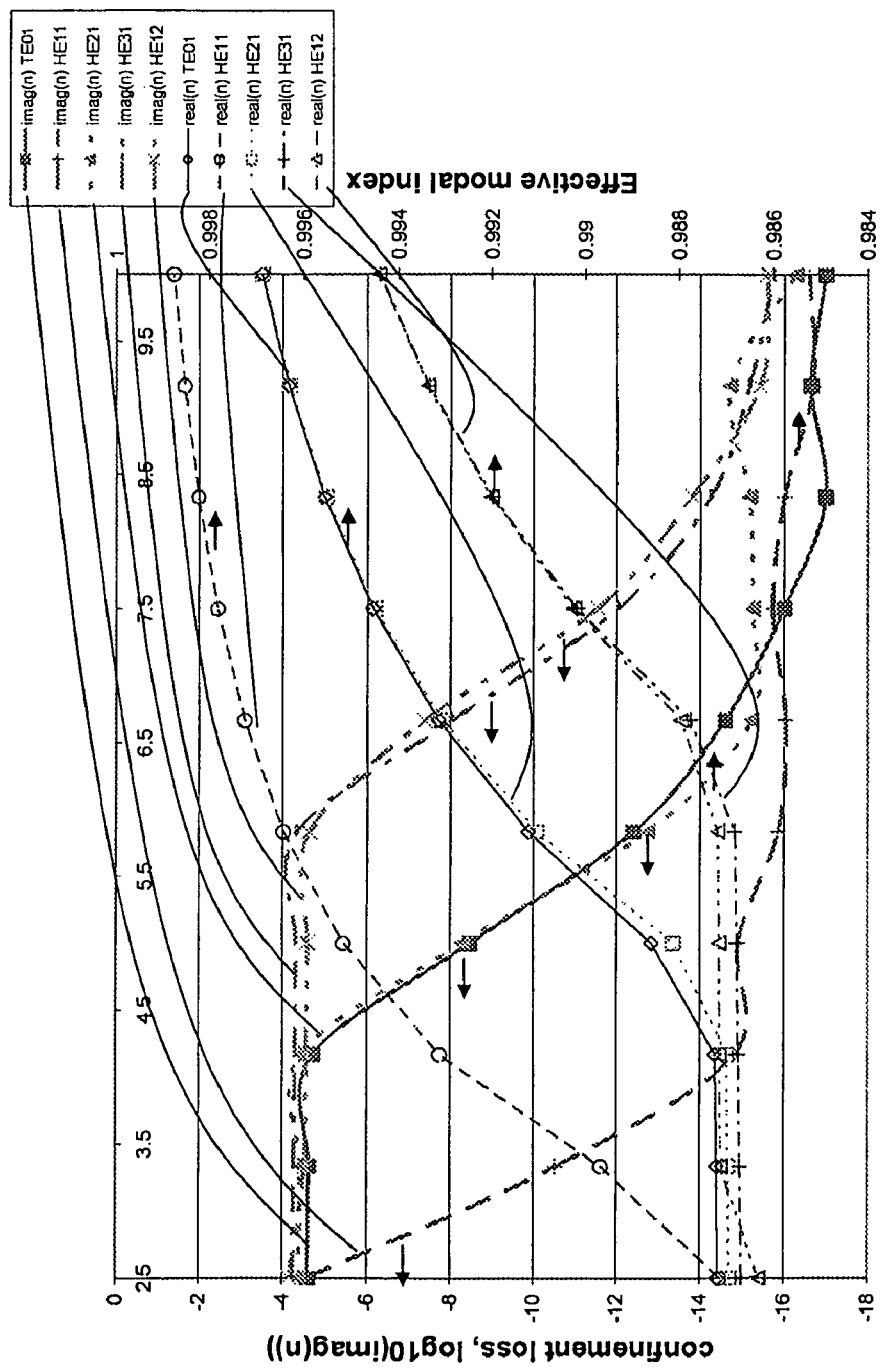
FIG. 12 is a plot of confinement loss and effective modal index versus core radius for a Bragg fiber.

FIG. 12 illustrates the number of modes supported in a Bragg fiber for various core radii by calculating the confinement loss as well as the effective indexes of various modes. As shown, low transmission loss can be realized for all the modes simulated when the core radius larger than 10 μm. At core radius between 4 μm and 5 μm, only HE11 mode is well supported. Below a core radius of 4 μm, all modes have high loss. This data indicates an optimum core size for single mode operation.

Before proceeding to the following analysis, additional definition of parameters is given below.

$n_r$: real part of effective index $n_i$: imaginary part of effective index

λ: optical wavelength v: normalized frequency k: =2π/λ, vacuum wave number

β: =$\beta_r$+i$\beta_i$=2π($n_r$+i$n_i$)/λ, propagation constant

α: =2πi$n_i$/λ, confinement loss $k_h$: =$k(n_h^2-n_r^2)^{1/2}$, transverse wave vector in the high index media $k_l$: =$k(n_r^2-n_l^2)^{1/2}$, transverse wave vector in the low index media m: order of transmission or stop bands, m∈(1, ∞)

In certain preferred embodiments of PBGF, the effective index $n_r$ of the guided mode is very close to the core refractive index $n_l$. This approximation leads to $k_l \approx 0$ and $k_h = k(n_h^2-n_l^2)^{1/2}$. In the limit of $n_r \approx n_l$, for TE-like modes, $$e^{ik_{TE}\Lambda} = \cos(k_h d) - \frac{k_h D}{2}\sin(k_h d) \pm \sqrt{\left[\cos(k_h d) - \frac{k_h D}{2}\sin(k_h d)\right]^2 - 1} \quad (4)$$

The amplitude of the $\exp(ik_{TE}\Lambda)$ determines the convergence or divergence of the modal field, the bandgap of the Bragg fiber are determined as:

$$|e^{ik_{TE}\Lambda}| < 1 \text{ transmission bands of the fiber} \quad (5)$$
$$|e^{ik_{TE}\Lambda}| \geq 1 \text{ stop bands of the fiber}$$

Since the amplitude of the $\exp(ik_{TE}\Lambda)$ provides a measurement of the degree of all TE-like mode confinement, this amplitude is proportional to the modal confinement loss. The transmission band boundary is determined by $|\exp(ik_{TE}\Lambda)|=1$. If a normalized frequency is define as $v=kd$ $(n_h^2-n_l^2)^{1/2}$ and in the limit of $n_r \approx n_l$, $v=k_h d$, then the upper limits of the transmission band are determined by $v_h=m\pi$, where m determines the order of the transmission band and is integer. Lower limits of the transmission bands (lower frequency limit) $v_l$ are determined by the following equation:

$$v\tan(v) = \frac{2R}{1-R} \quad (6)$$

Figure 13:
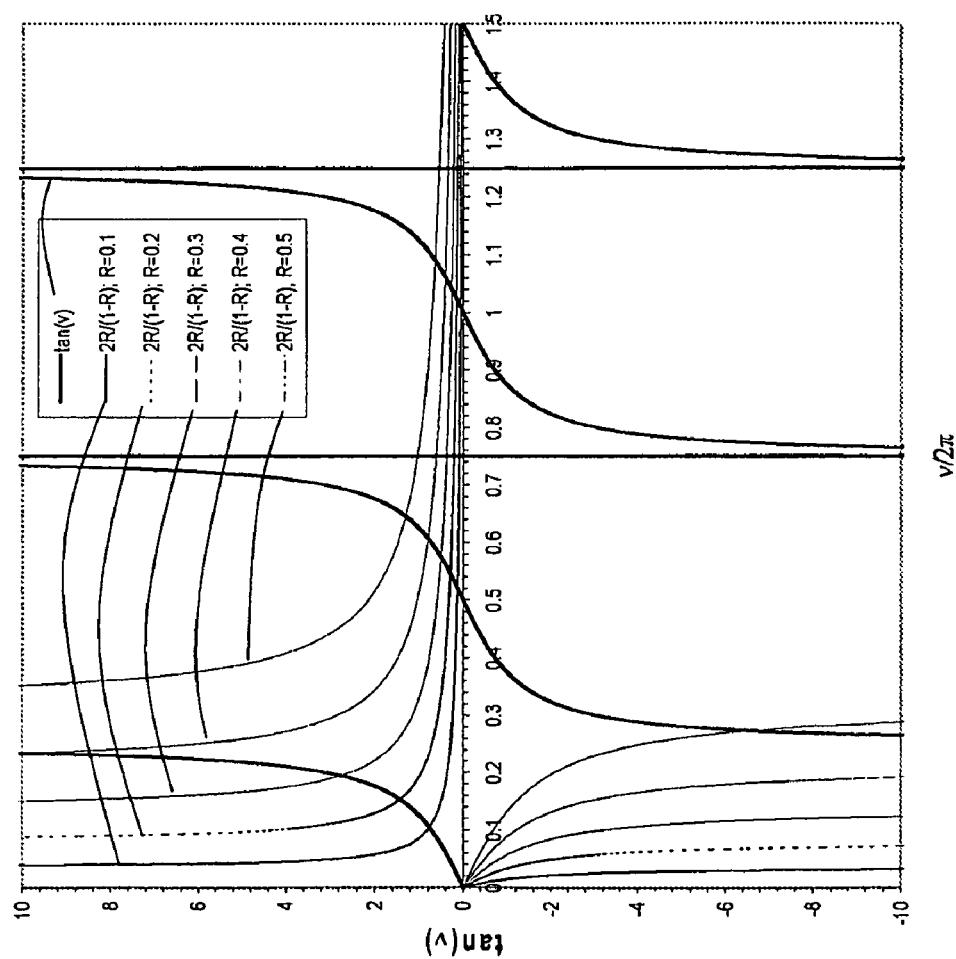
FIG. 13 schematically illustrates the calculations for determining transmission bands in a Bragg fiber.

FIG. 13 plots the $\tan(v)$ and $2R/(1-R)$ at various values. The intersection points determine lower transmission limits. Multiple transmission bands are consequence of the periodic nature of $\tan(v)$.

The upper transmission limits are independent of waveguide parameters and lower transmission limits depend only on R. As illustrated, the normalized frequency $v$ is only dependent on the dimensional parameter d and becomes independent of period, $\Lambda$. Accordingly, the period $\Lambda$ does not play a role in determining the limits of the transmission bands. The relationship for determining the lower limit of the transmission band is shown in FIG. 13. The ratio R plays a minor role in determining the lower limits of the transmission bands. Many transmission bands are spaced apart in normalized frequency $v$ by $\pi$. Furthermore, the lower transmission band limit increases with R. The transmission band gets narrower as the width of the low index layers get narrower.

The precise amount of confinement loss is determined by the modal field distribution, which is also influenced by the core design. $|\exp(ik_{TE}\Lambda)|$ is proportional to the confinement loss and is plotted in FIG. 14 against the normalized frequency $v$ for five different R values. Three transmission bands are shown. As illustrated, the upper transmission limits are independent of R, while the lower limits of the transmission bands are related to R. Smaller R leads to wider transmission bands and lower confinement loss. High order transmission bands have lower confinement loss.

Figure 14:
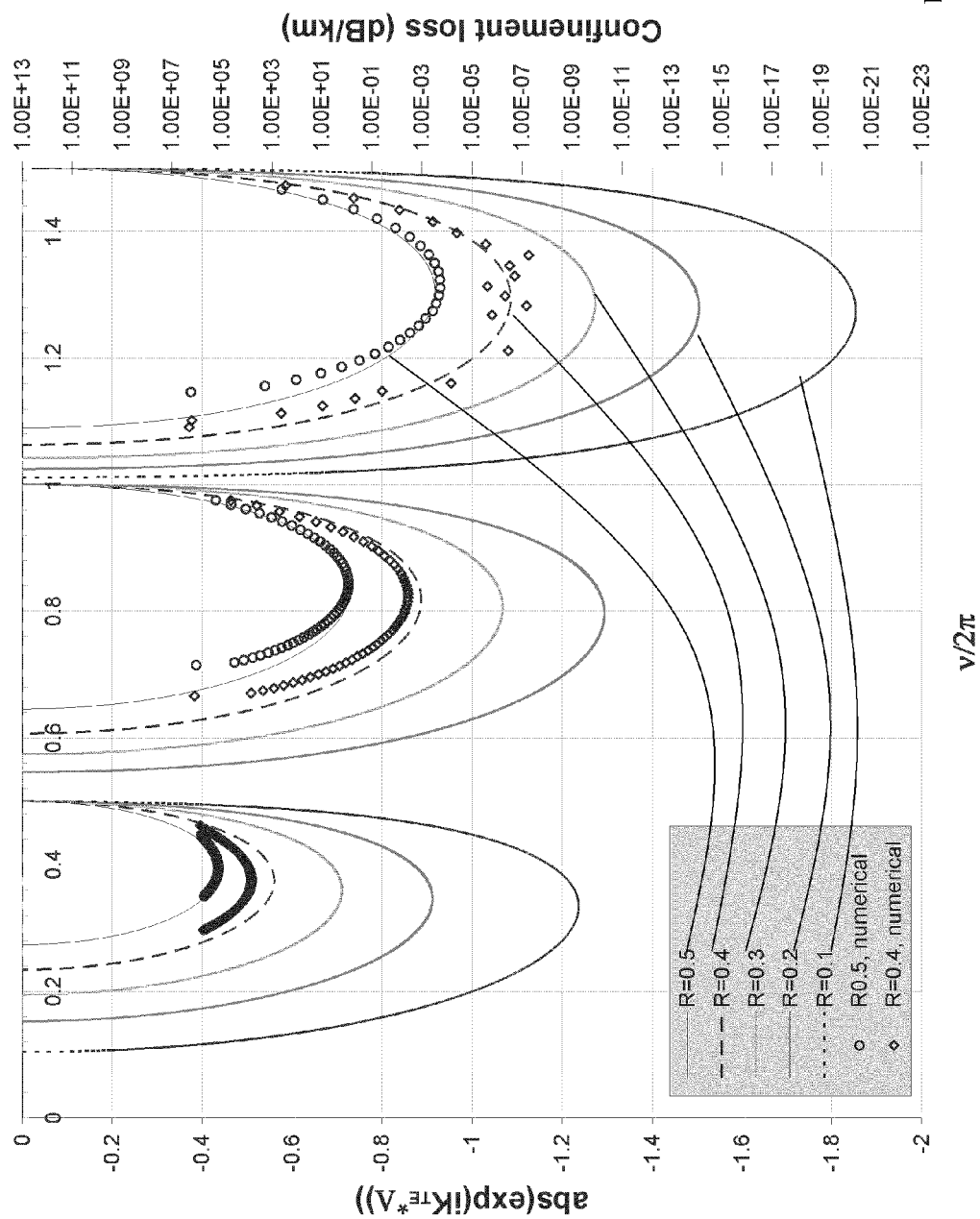
FIG. 14 schematically illustrates a comparison of the confinement loss determined using the analytic formula and full numerical calculation.
Figure 16:
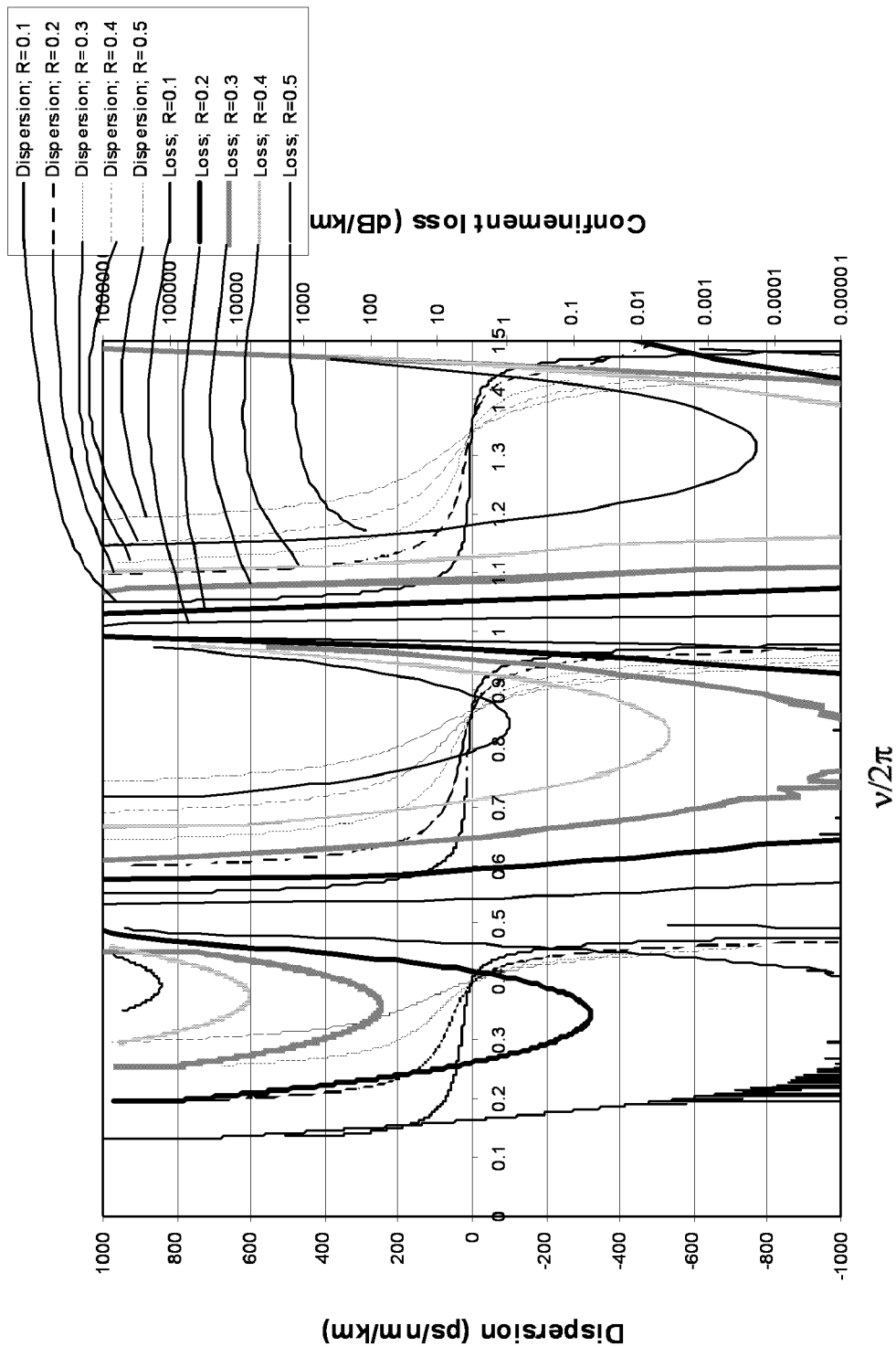
FIG. 16 is a plot of dispersion and confinement loss versus normalized frequency showing the effect of the ratio of the thickness and period (d/Λ) of the high index regions for a Bragg fiber.

The numerical simulations for R=0.4 and 0.5, are shown in FIG. 14 in by dots. As shown, the numerically calculated confinement loss fits well with the simple formulation presented herein with some adjustment of scale factor. The full numerical results are shown in FIG. 16 for all the R values plotted against the normalized frequency $v$. As shown, the confinement loss calculated by the numerical model is also consistent with the formulation described herein.

Figure 15:
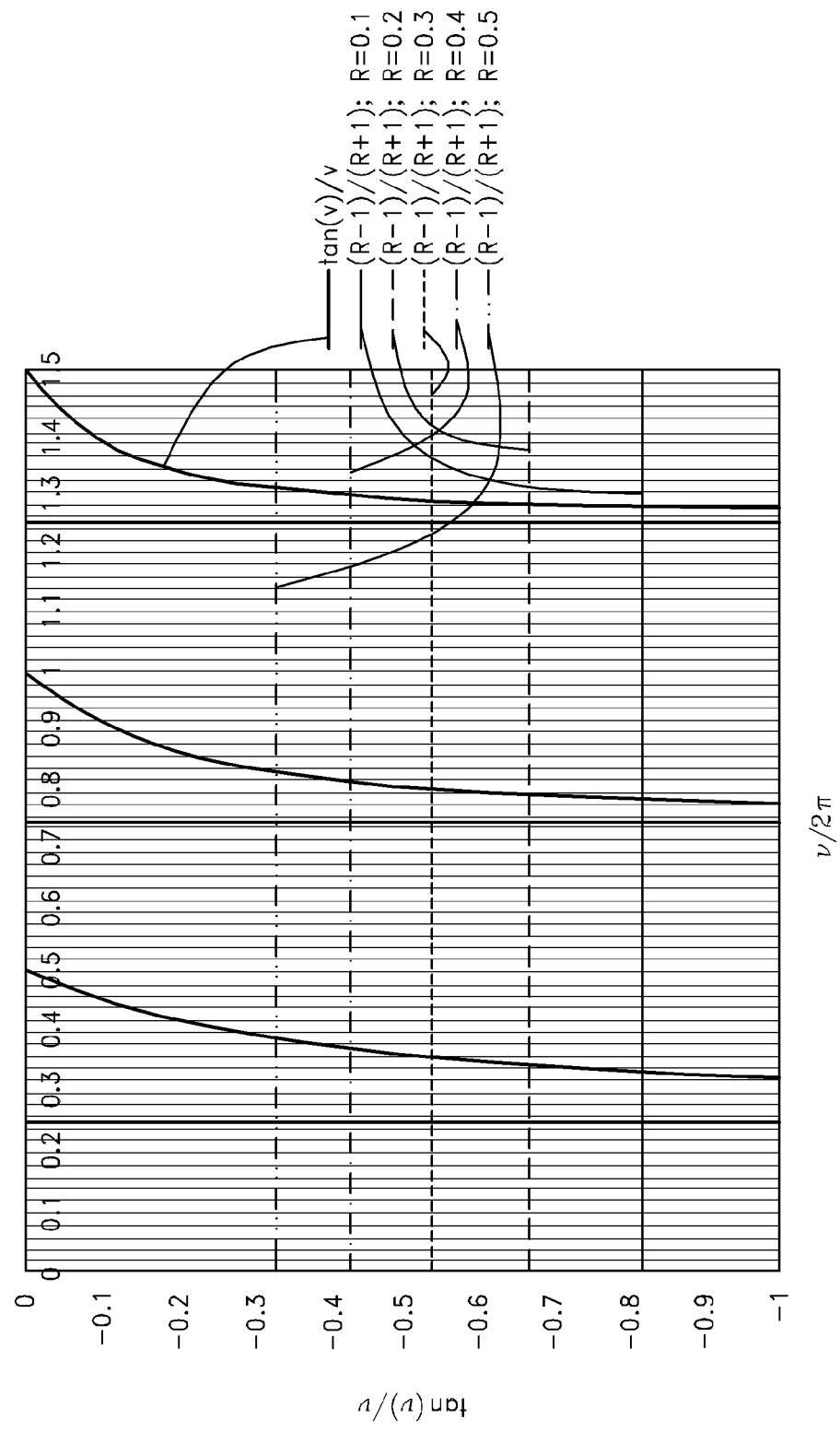
FIG. 15 schematically illustrates the formula for determining minimum transmission loss in a Bragg fiber.

FIG. 15 plots $\tan(v)/v$ and $(R-1)/(R+1)$ at various values. The intersection points determine minimum transmission. The transmission minimums in FIG. 15 happen at $v_{opt}$, which is determined by:

$$v\tan(v) = \frac{R-1}{R+1} \quad (7)$$

Two sides of above equation are plotted in FIG. 15. $(R-1)/(R+1)$ is plotted for various R values. The intersection determines the minimum transmission points, which dependent on R. The transmission minimum moves towards high $v$ with an increase of R.

Since the simple method of determining transmission bands is based on TE-like modes, this method applies to all the TE and HE modes. The equivalent formulae for TM and HM modes are:

$$e^{ik_{TM}\Lambda} = \cos(k_h d) - \frac{n_l^2 k_h D}{2n_h^2}\sin(k_h d) \pm \sqrt{\left[\cos(k_h d) - \frac{n_l^2 k_h D}{2n_h^2}\sin(k_h d)\right]^2 - 1} \quad (8)$$

The uppers limit of the transmission bands are given by $v_h=m\pi$ while the lower limit of the transmission band is determined by $$v\tan(v) = \frac{n_h^2}{n_l^2}\frac{2R}{1-R} \quad (9)$$

Figure 17:
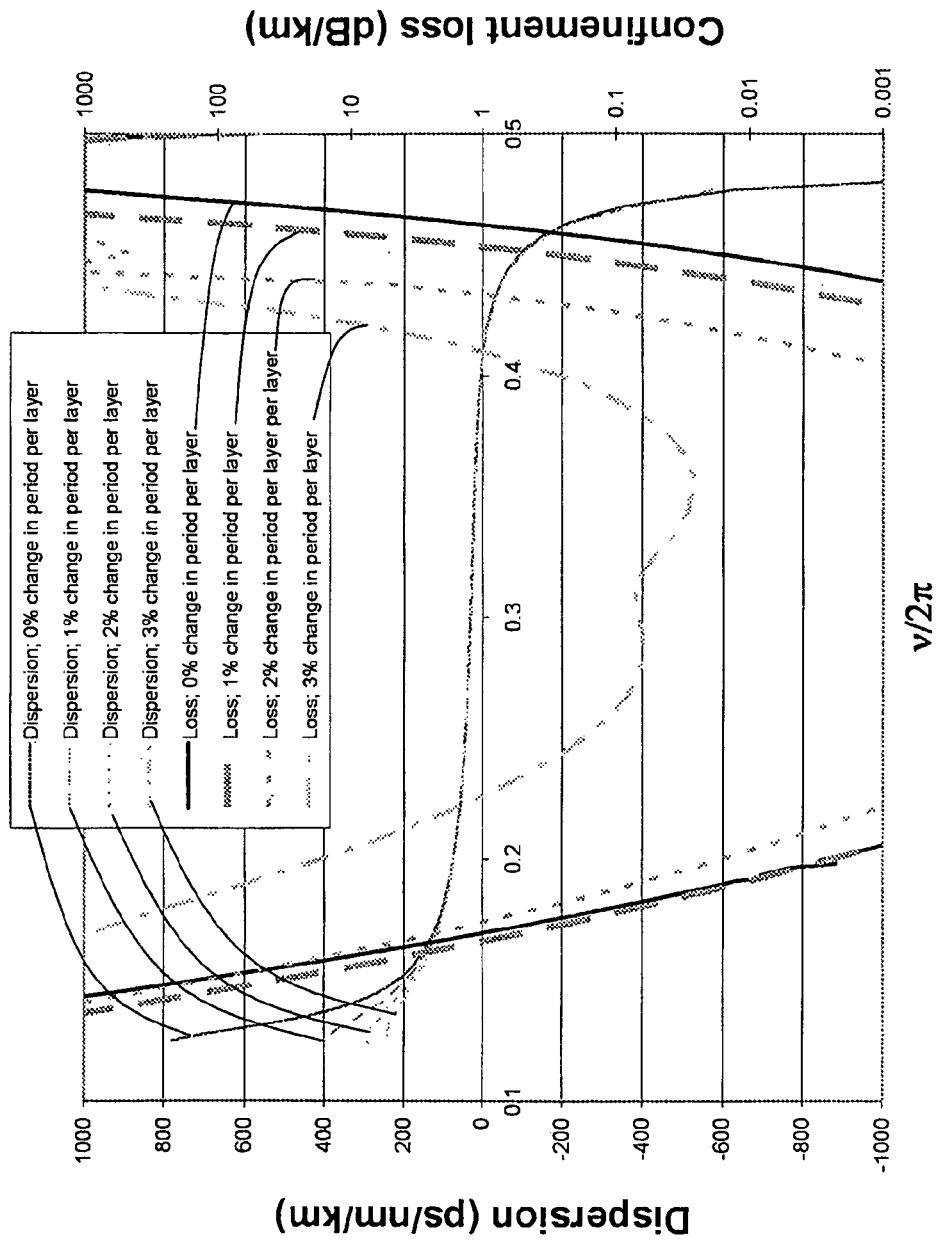
FIG. 17 is a plot of dispersion and confinement loss versus normalized frequency showing the effect of chirps in a Bragg fiber where only the period, Λ, of the high index ring-like regions is varied while the width, d, is kept constant.

Full numerical simulation was performed for cases where d is kept constant while $\Lambda$ is changed in an incremental fashion from the innermost layer. The results are shown in FIG. 17 for the first transmission band. With below 2% change in period per layer, the transmission bands are substantially unchanged. Above 3% change in period per layer, the transmission band getters shallower and narrower. This transmission band reduction and transmission loss increase is due to the outer layers no longer providing good confinement in phase with the inner layers. This effect is the result of the assumption that $n_r \approx n_l$ in deriving equations 6 & 7. This assumption makes $k_j=0$ and D irrelevant. In practice, $n_r$ is close to but not equal to $n_l$, so that the Bragg fiber characteristics have a weak D dependence. As demonstrated in FIG. 17, large variation of D will reduce transmission bandwidth and increase transmission loss.

Note that with a 3% change in period per layer, the period of the outmost layer is 30% larger than that of the innermost layer.

Figure 18:
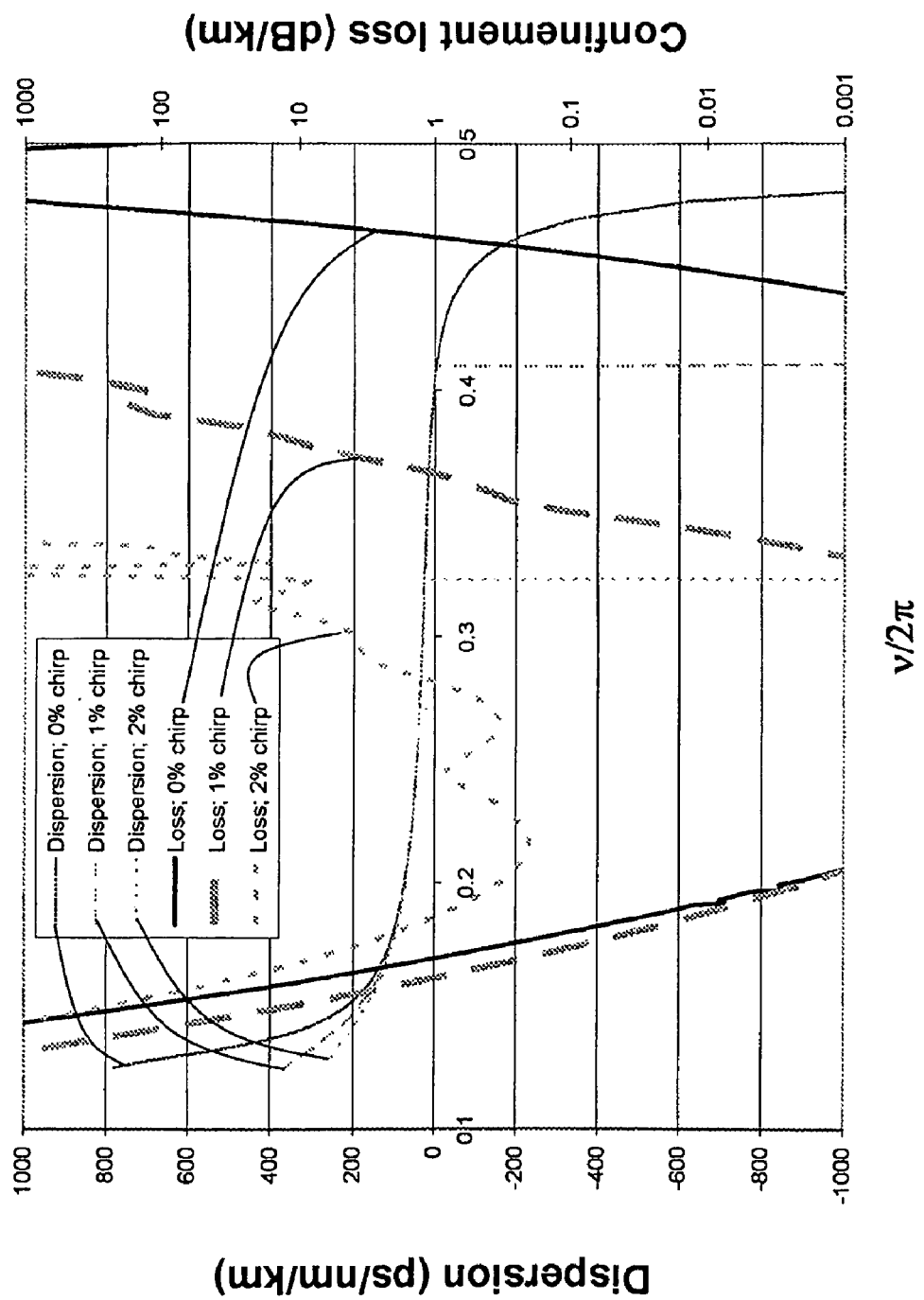
FIG. 18 a plot of dispersion and confinement loss versus normalized frequency showing the effect of different chirps in a Bragg fiber where both the average width, d, and period, Λ, are varied.

Another simulation was run for the same fiber with various chirps, i.e. both d and $\Lambda$ are changed incrementally form innermost layer. The results are shown in FIG. 18. Even at 1% of chirp, the upper transmission limit is significantly changed. At 2% chirp, the transmission band is substantially weakened and narrowed.

Based on these results, both d and D are kept constant from layer to layer in various preferred embodiments, so as to provide increased or maximum transmission bandwidth and reduced or minimum transmission loss. Using a constant value of d appears to have a stronger effect than using a constant value of D. For the same reason, a constant d and D around each circumference is also use in certain embodiments. For example, in a triangularly stacked claddings, variation of both d and D around each layer surrounding the core can lead to a reduction of overall transmission bandwidth and an increase of transmission loss comparing with a Bragg fiber. In certain embodiments, however, d and/or D are varied.

FIGS. 17 and 18 show that the outer cladding layers have less influence on dispersion properties. The most significant impact of the chirp is reduction of transmission window. Dispersion is changed little in fibers where the inner most layer is identical.

In these simulations of Bragg fibers, the impact of surface modes, which will further reduce the transmission bandwidth, has been ignored. As discussed above, in a design that excludes surface modes, $V=2\pi\delta^*(n_h^2-n_l^2)^{1/2}/\lambda<0.5$, where $\delta$ is the maximum thickness of the core/cladding layer. FIG. 14 shows that a small R allows a wide transmission bandwidth. The widest possible transmission bandwidth in wavelength domain is when $v$ is from $v_l$ to $v_h=\pi$, i.e. $\lambda$ from $\lambda_{min}=2d(n_h^2-n_l^2)^{1/2}$ to $\lambda_{max}=2\pi d(n_h^2-n_l^2)^{1/2}/v_l$, where $v_l$ depends on R and is given by equation 6. The upper wavelength limit $\lambda_{max}$ is a result of loss of confinement when $v$ is too small. The lower wavelength limit $\lambda_{min}$ is a result of the existence of tunneling process in the cladding. A smaller d would give a lower transmission band limit $\lambda_{min}$.

The lowest loss can be achieved in the absence of surface modes when operating at the highest possible m and at $v=v_{opt}$. However there will be more surface modes at higher m. This fact typically limits the highest possible m to operate. A smaller core/cladding thickness $\delta$ will allow operation at higher m without the penalty of the surface modes, hence lower possible transmission loss. Note, however, that the transmission band gets narrower in the wavelength domain as m increases.

The results of FIG. 14 pertain to a Bragg fiber where there is uniform d and D circumferentially. In a general situation where d is not uniform, e.g. in the case of triangularly stacked cladding, the minimum loss will no longer occur at $v=v_{opt}$ as determined by equation 7 and the shape of the transmission band in FIG. 14 will no longer apply. Nevertheless, the effect can be studied by considering the effect of a summation over a range d and D. The effective maximum transmission band will narrow and minimum transmission loss will increase, but there will still be a lowest loss at a new optimum $v=v_{opt}$. It is therefore better in certain embodiments to use a cladding geometry having a substantially uniform d and D.

The cylindrically stacked cladding designs illustrated in FIGS. 4A and 4B are similar to the Bragg fiber illustrated in FIG. 3A and FIG. 6 when drawn into optical fibers. The holes will be slightly pressurized during fiber drawing. This will lead to a disappearance of the gaps between tubes in FIG. 4A. As discussed above, FIG. 4G illustrates an example of such a drawn fiber. The hole boundaries will be joined to form concentric circular layers 431 centered about the center of the structure. The circular layers or rings 431 will be linked between them by webs 433 formed from part of the hole boundaries. The fiber 430 also includes concentric rings 435 comprising the circular arrangement of evacuated or gas or air filled openings.

Accordingly, the PBG fibers formed from microstructures arranged in a circular pattern are similar to a Bragg fiber. Both comprise substantially ring-shaped regions of high and low refractive index. These substantially ring-shaped regions of high and low refractive index are concentric and are centered about the core. These substantially ring-shaped regions of high and low refractive index alternate.

In the case where the PBG fiber comprise cladding formed by a plurality of microstructures such as shown in FIGS. 4E and 4F, the average thickness, d, of the high index regions may be calculated between centerlines through the low index regions. These centerlines pass through the centers of the microstructures forming the low index region. In the case where the low index regions are circular or annular, these centerlines will also be circular or annular as the microstructures are arranged along circular or annular paths. Example centerlines A, B are shown in FIG. 4F. In general, the spacing between the two centerlines corresponds to the pitch, $\Lambda$.

The average thickness of the high index material between these two centerlines A, B may be computed in different ways. One method of determining this average thickness is to calculate the area of the high index material located within these two centerlines A, B. This area can be uniformly distributed along an annular pathway that extends around the core between and equidistant to the two circular or annular centerlines. The width of this annular pathway between the two centerlines corresponds to the average thickness of the high index material, d. This average thickness is computed for the other rings of high index material in a similar fashion to obtain a thickness, d, that an average across the cladding. Other ways of calculating the average thickness of the high index material between the two centerlines may also be used.

The same approach for determining the average thickness of the high index material is applicable ring-shaped regions of high index having other shapes as well. In the case, for example, where the microstructures are arranged to form hexagonal rings, the centerlines are hexagonal as the centerlines pass through the centers of the microstructures forming the ring. The thickness of the high index material between these hexagonal centerlines may be determined to obtain the value, d. The same approach can be used for any arbitrary shaped regions of high index material and is not limited to circular or hexagonal shapes.

A similar approach can be used to determine the average thickness, $\delta$, of the innermost high index region closest to the core. The average thickness of the high index material within the centerline through the ring of microstructures closest to the core is determined. In FIG. 4F, for example, centerline A is used. In one method, the area of all the high index material within this first centerline, A, is computed and uniformly distributed along an annular pathway adjacent to and bounded by the first centerline. Accordingly, the outermost border of this annular pathway will generally pass through the center of the microstructures in the first ring. The thickness of this annular pathway corresponds to the average thickness, $\delta$. As discussed above, the average thickness of hexagonal or other shaped rings may be computed in this manner as well. One skilled in the art will know how to determine the average thicknesses, d and $\delta$, of the high index material based on the description provided herein.

The low transmission loss and low dispersion over a wide wavelength region of several hundred nanometers as illustrated in FIG. 9 is very useful for wavelength-division-multiplexing systems for telecommunications, where tens to hundreds of channels, each at a different wavelength, can be sent over a single optical fiber. In addition, such systems also have a much reduced nonlinearity due to most of the guided light being in gas or vacuum. This feature allows higher power to be launched and consequently higher transmission rate and/or longer transmission distance without amplification.

Figure 19:
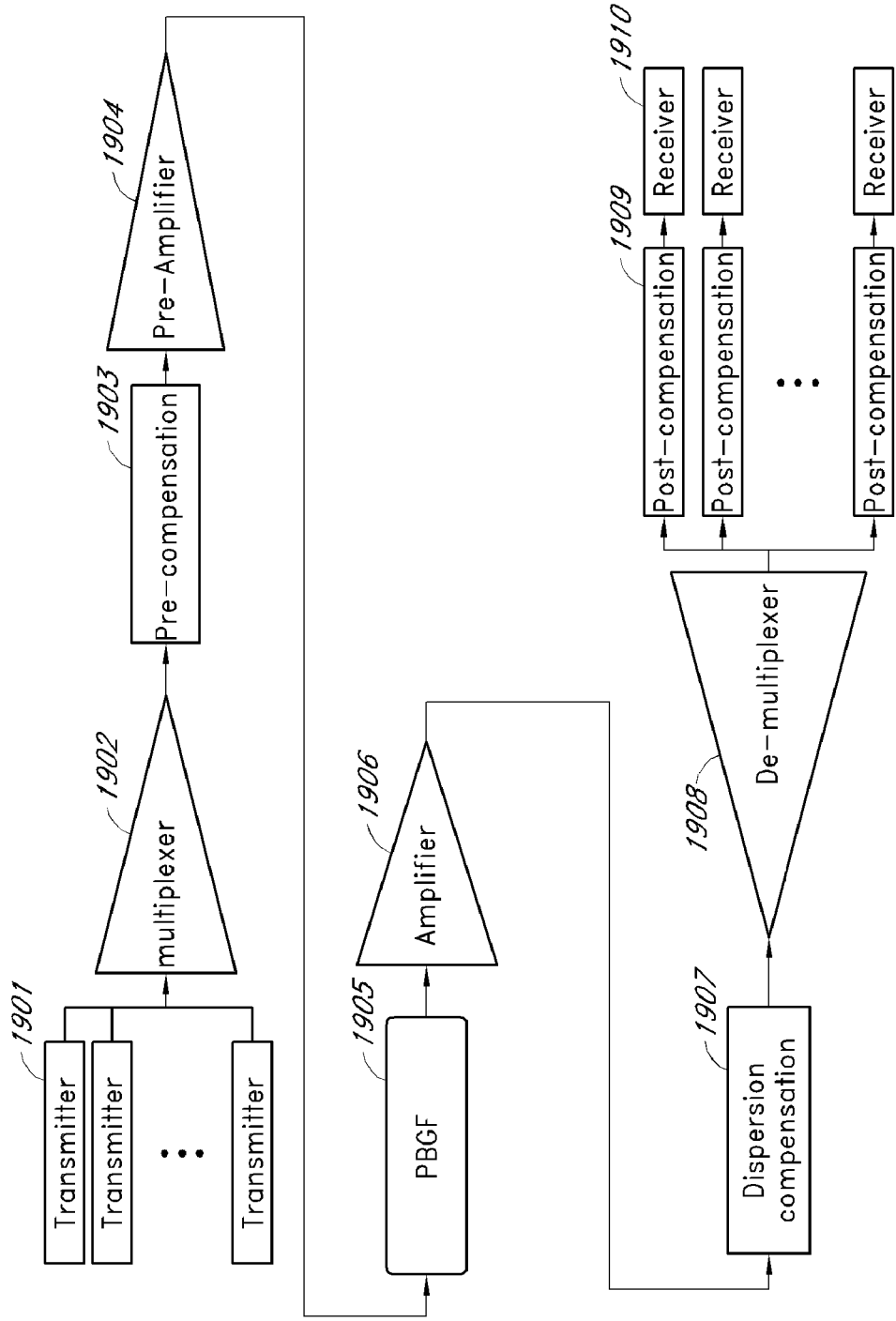
FIG. 19 is a block diagram schematically illustrating a single span telecommunication system incorporating a PBGF.
Figure 20:
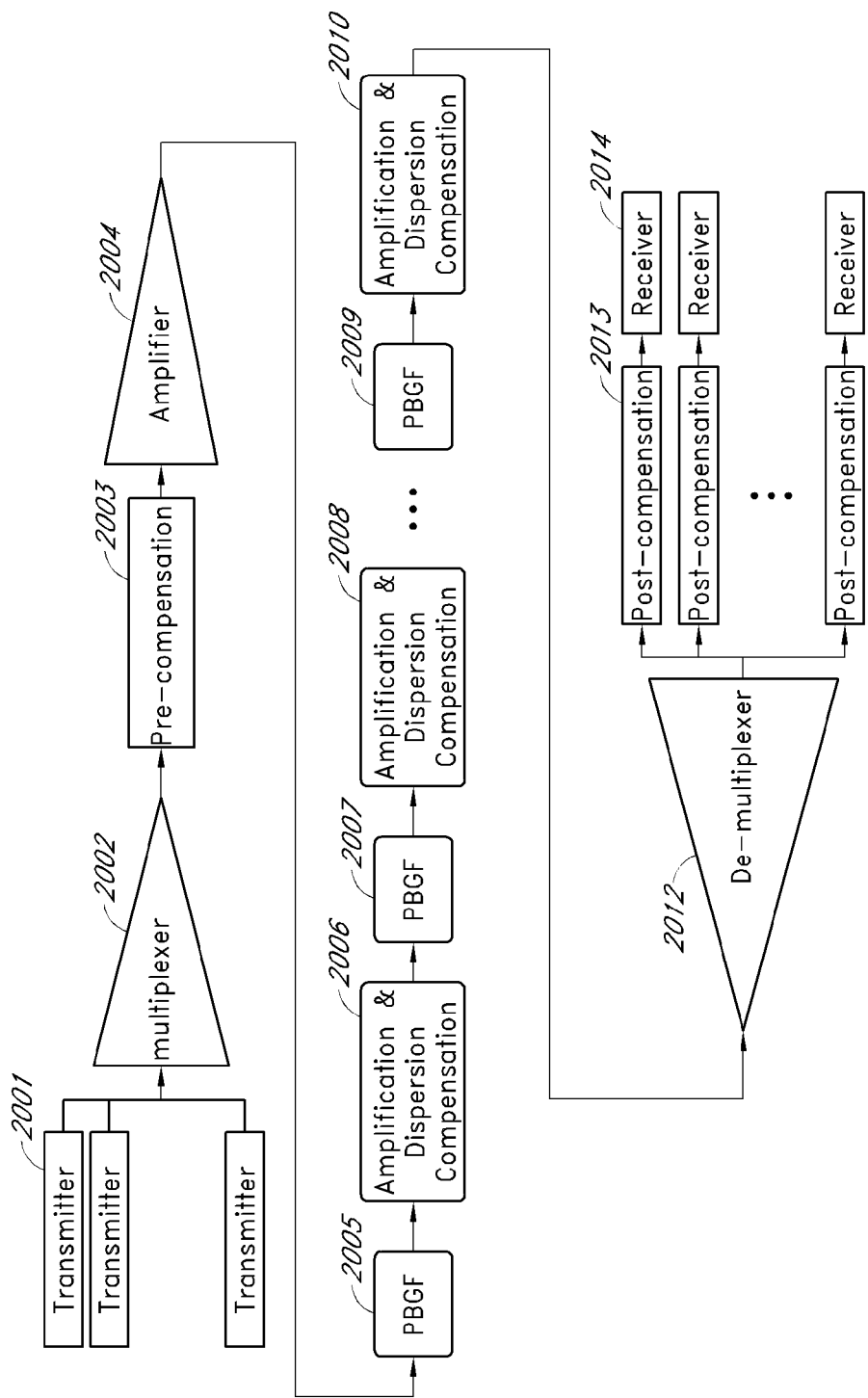
FIG. 20 is a block diagram schematically illustrating a multiple span telecommunication system incorporating PBGFs.

FIG. 19 illustrates such a telecommunication system incorporating a PBGF 1905. Signals from transmitters 1901 are multiplexed by a multiplexer 1902 and are then pre-compensated by a dispersion pre-compensation unit 1903 and amplified by an amplifier 1904. A single span of PBGF 1905 is used for transmitting the signals over a distance from source to destination. The transmitted signals are then amplified at the destination by an amplifier 1906. A dispersion compensation unit 1907 is used before the de-multiplexer 1908. Each signal is finely compensated by post-compensation unit 1909 to take out any channel dependent transmission distortion before receipt by a plurality of receivers 1910. FIG. 20 illustrates a similar transmission system that also includes transmitters 2001, a multiplexer 2002, a pre-compensation unit 2003 and an amplifier on the source end and a demultiplexer 2012, a plurality of post-compensation units 2013 and receivers 2014 on the destination end. In the system shown in FIG. 20, however, multiple spans of PBGF 2005, 2007, 2009 are included. Additional dispersion compensation units and amplifiers 2006, 2008, and 2010 in each span are also included. Optical connection is provided between the optical components as shown in FIGS. 19 and 20, although structures may be included between these optical components as well. A variety of these components may comprise optical fiber. FIGS. 19 and 20 only show the key components of a telecommunication system. Additional components can be added. Likewise, some components in FIGS. 19 and 20 can be omitted and/or locations changed in different embodiments. Other configurations and variations are also possible.

PBGF can also be employed in systems for generating optical pulses such as ultrafast optical pulses. Additional details regarding ultrafast pulse systems is included in U.S. patent application Ser. No. 10/814,502 entitled "Pulsed Laser Sources" and U.S. patent application Ser. No. 10/814,319 entitled "High Power Short Pulse Fiber Laser", which are incorporated herein by reference in their entirety.

Figure 21A:
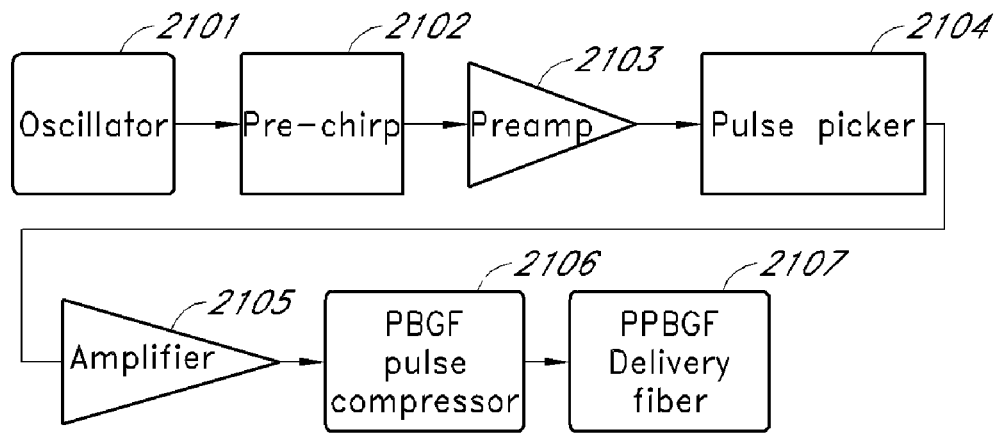
FIGS. 21A and 21B are block diagrams schematically illustrating fiber chirped pulse amplification systems incorporating PBGFs.
Figure 21B:
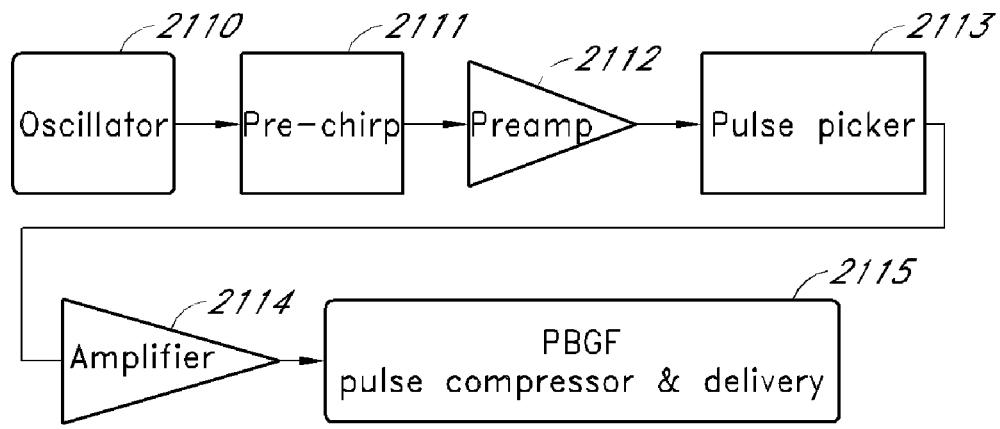

FIG. 21A, for example, illustrates a fiber chirped pulse amplification (FCPA) system incorporating a dispersion tailored PBGF 2106. Pulses from oscillator 2101 are pre-chirped by using a pre-chirp unit 2102 and are then amplified by a pre-amplifier 2103. Pulse picker 2104 can be used to pick a subset of pulses, which are then amplified by main amplifier 2105. The PBGF 2106 is used to compress the amplified pulses, which are subsequently delivered by a low dispersion PBGF delivery fiber 2107. Optical connection is provided between the optical components as shown in FIG. 21A although structures may be included between these optical components as well. A variety of these components may comprise optical fiber or optical fiber devices. In FIG. 21B, also shows a fiber pulse amplification system comprising an oscillator 2110, a pre-chirp unit 2111, a preamplifier 2112, a pulse picker 2113, a main amplifier 2114. In FIG. 21B, however, the PBGF compressor and delivery fiber are combined into a single fiber 2115. FIGS. 21A and 21B only show the key components of a pulse amplification system. Additional components can be added. Likewise, some components in FIGS. 21A and 21B can be omitted and/or locations changed in different embodiments. Other configurations and variations are also possible.

Figure 22A:
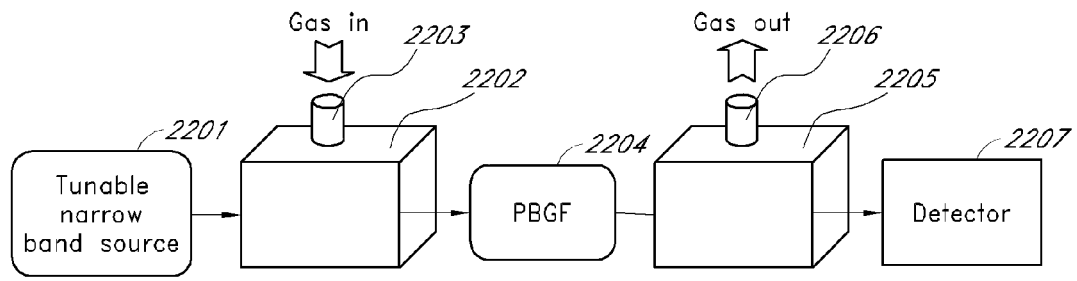
FIG. 22A is a block diagram schematically illustrating a gas detection system based on spectral transmission measurement using a PBGF.

A PBGF with low loss and a wide transmission band can also be used for trace gas analysis with much improved sensitivity due to the long interaction length. FIG. 22A illustrates such a system that detects, identifies, quantifies, or otherwise performs measurements on gases based on spectral absorption. A tunable source 2201 is optically coupled to a PBGF 2204 through a multiplexer 2202, which allows gas to be injected into the core of the PBGF 2204. A gas filter 2203 may be employed to take out solid particles in the gas stream. At the output end, a de-multiplexer 2205 is used to separate gas and the optical beam. The optical beam is then directed to a detector 2207. Gas pumps can be connected to gas filter 2203 and/or gas outlet 2206 to speed up gas flow.

Figure 22B:
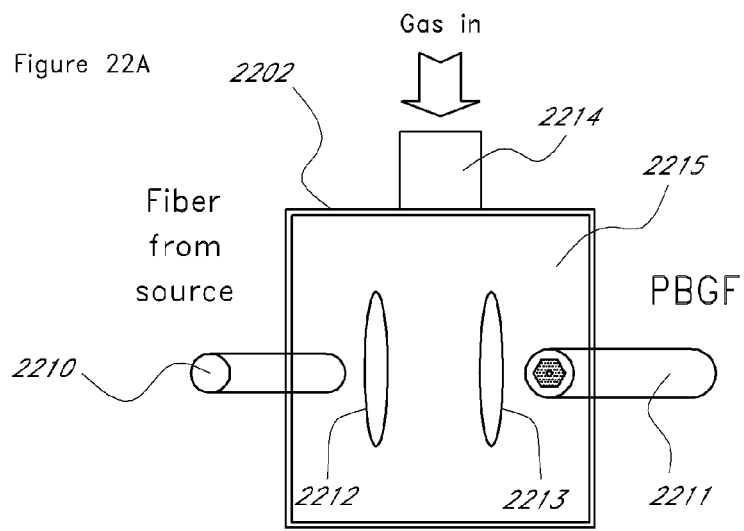
FIGS. 22B and 22C are schematic drawings of a multiplexer and a demultiplex, respectively, for combining and separating the gas and the light in the gas detection system of FIG. 22A.
Figure 22C:
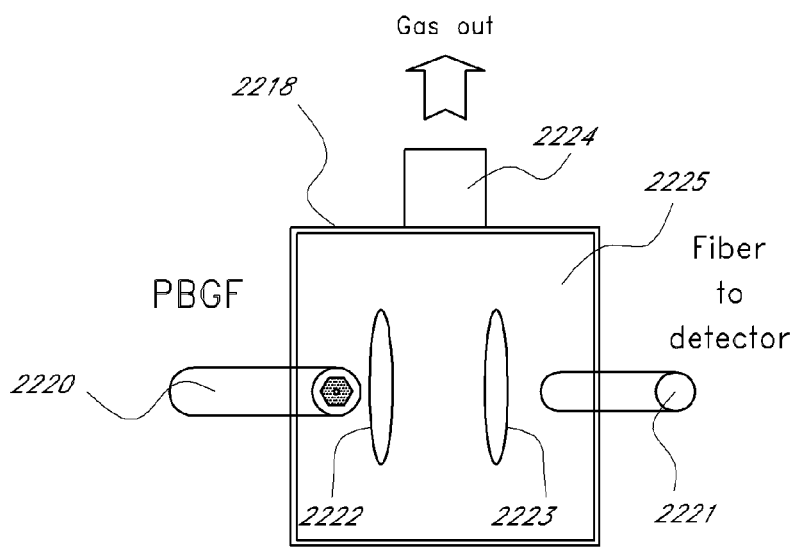

FIG. 22B illustrates a configuration of the multiplexer 2202 comprising a sealed chamber 2215. Source light propagated by a fiber 2210 is collimated by a collimating lens 2212 and focused by lens 2213 into an input end 2211 of the PBGF 2204. Gas is input in through a gas input 2214 which may comprise a filter as described above. The de-multiplexer 2205 is illustrated in FIG. 22C. The de-multiplexer also comprises a chamber 2218, an output end 2220 of the PBG fiber 2204 as well as a collimating lens 2222 and a focusing lens 2223 which receives the light output from the output 2220 of the PBGF 2204 and couples the light into an output fiber 2221. The demultiplexer 2205 further comprises a gas output port 2224. A broad band source and a monochromator can be used instead of the tunable light source 2201 in FIG. 22A.

In such a system gas is introduced into the multiplexer and enters into portions of the PBGF though holes or openings therein. In various preferred embodiments, the core is hollow and the gas enters the hollow core. The gas affects the propagation of the light, for example, by attenuating the light due to absorption at one or more wavelengths. The absorption spectrum of the gas can, therefore, be measured using the detector 2308 and monochrometer or tunable filter 2307. In certain embodiments such as shown in FIGS. 22A-22C the gas is flowed through the PBGF 2204. In such cases, the long length of the fiber 2204 may increase the interaction of the gas with the light and provide a higher signal. In other embodiments, other properties of the light may be measured.

Figure 23A:
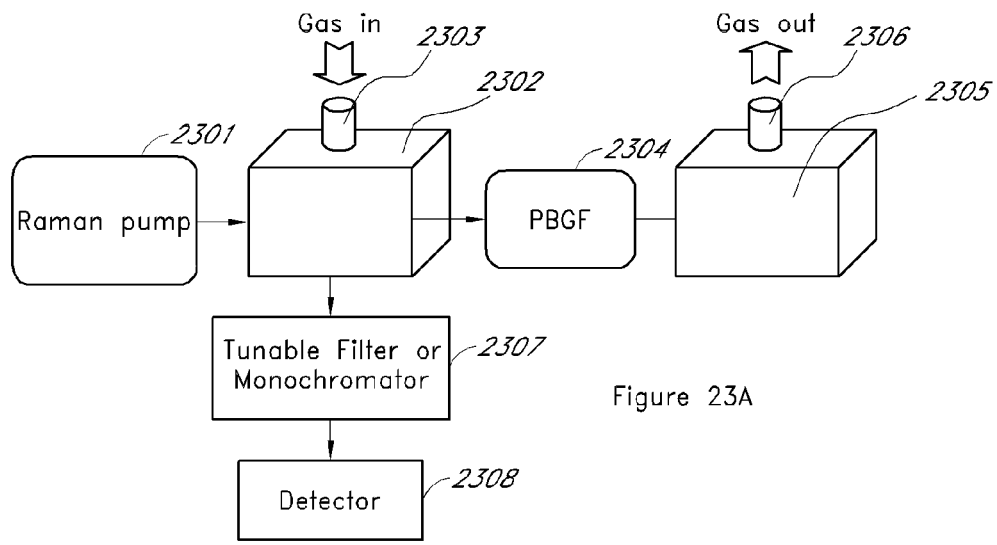
FIG. 23A is a schematic illustration of a gas detection system based on backward Raman scattering in a PBGF.

FIG. 23A, for example, illustrates a trace gas detection system based on detection of Raman scattered light. The gas is introduced into the fiber and causes Raman scattering which is measured. The gas may enter openings in the fiber and may, in certain preferred embodiments, flow through the hollow core of the PBGF. As described above, the long interaction length of the PBGF provides increased detection sensitivity. An additional advantage is that a large part of the Raman-scattered light is collected and can also propagate within the photonic bandgap fiber. This feature is especially true for PBGF with a wide transmission band, i.e. larger solid collection angle.

In the embodiment shown in FIG. 23A, a Raman pump 2301 is optically coupled through a multiplexer 2302 to a PBGF 2304. An output end of the PBGF 2304 is optically coupled to a de-multiplexer unit 2305. Gas enters through a filter 2303 that removes solid particles. Gas exits through the outlet 2306 on the de-multiplexer. Pumps can be used at the inlet 2303 and the outlet 2306 to speed up gas flow. Back-propagating scattered light by Raman scattering is directed towards a tunable filter or a monochromator 2307 and onto the detector 2308. The tunable filter or monochromator 2307 and detector 2308 can measure the wavelength spectrum of the scattered light.

Figure 23B:
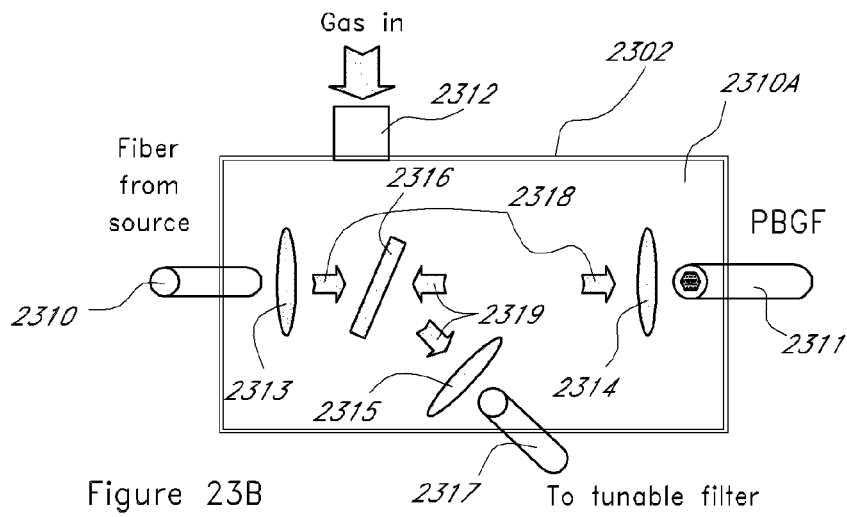
FIGS. 23B and 23C are schematic drawings of a multiplexer and a demultiplex, respectively, for combining and separating the gas and the light in the gas detection system of FIG. 23A.

The multiplexer 2302 comprising a sealed chamber 2310A is illustrated in FIG. 23B. Pump light is carried in by an optical fiber 2310 optically coupled to the pump source 2301 and is then collimated by a collimating lens 2313. The collimated pump beam 2318 is focused by a focusing lens 2314 into an input end 2311 of the PBGF 2304. A back-propagating scattered Raman signal 2319 is reflected by a filter 2316, which is designed to only reflect Raman signal but not the pump light. The Raman signal 2319 is focused by a focusing lens 2315 onto an output fiber 2317 optically connected to the tunable filter or monochromator. Gas enters in through an gas inlet port 2312 which may comprise a filter.

Figure 23C:
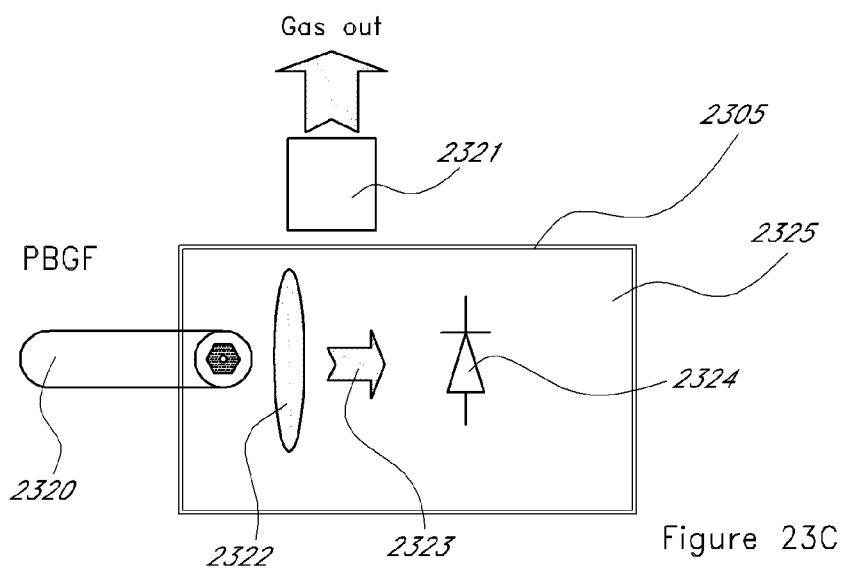

The de-multiplexer 2305 is illustrated in FIG. 23C. The de-multiplexer 2305 comprises a sealed chamber 2325 and a collection lens 2322 that collect pump light from an end 2320 of the PBGF 2304. The de-multiplexer further comprises a detector 2324 for monitoring the pump light that propagates through the PBGF 2304. The collection lens 2322 couple the pump light from the end 2320 of the PBGF 2304 and directs the pump light onto the detector 2324.

Figure 24A:
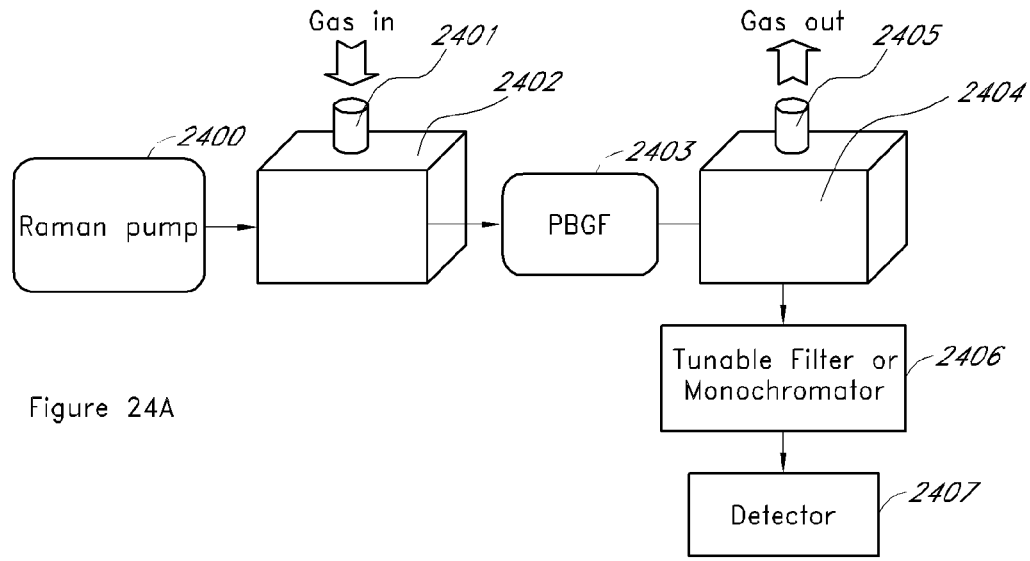
FIG. 24A is a schematic illustration of a gas detection system based on forward Raman scattering in a PBGF.

FIG. 24A shows a Raman detection system based on detection of a forward propagating Raman signal. In certain preferred embodiments, operation is in the stimulated Raman regime, where much stronger signal is expected due to amplification in the presence of high pump power. The configuration shown in FIG. 23A can also be used in a stimulated Raman mode to detect stimulate Raman emission.

The Raman detection system shown in FIG. 24A comprises a Raman pump 2400, a demultiplexer 2402 having a gas input port 2401, a PBG fiber 2403, and a demultiplexer 2404 having a gas output port 2405. The system further includes a tunable filter or monochromator 2406 optically coupled to the demultiplexer 2404 so as to receive the Raman signal therefrom. A detector 2407 is also included to sense the Raman signal.

Figure 24B:
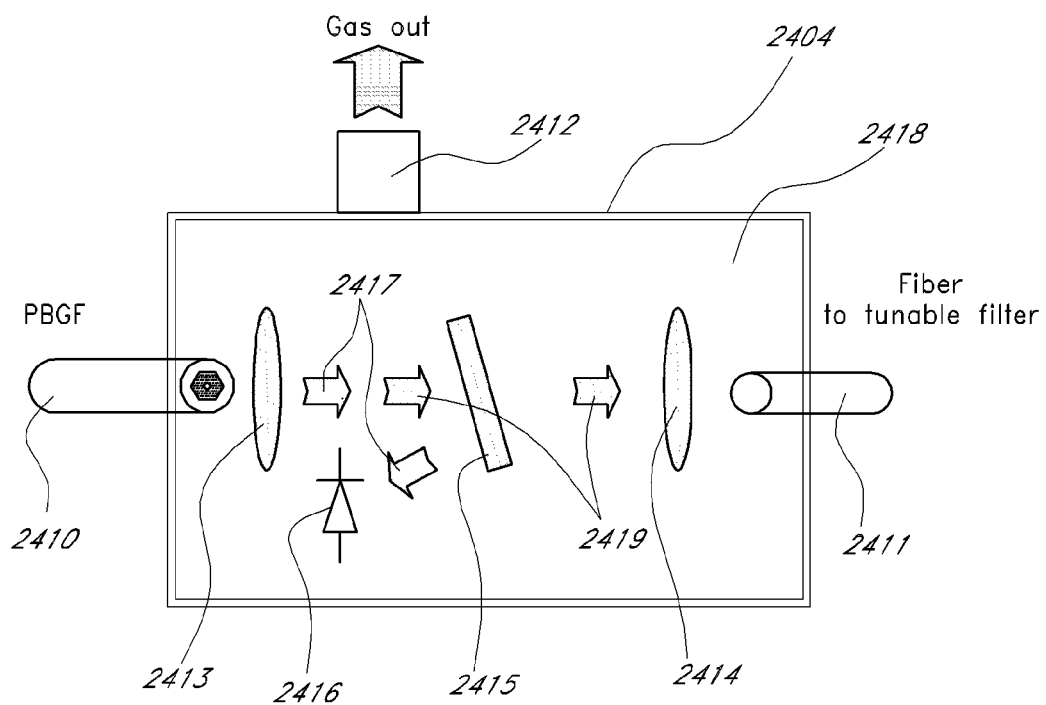
FIG. 24B is a schematic drawing of a demultiplex for separating the gas and the light in the gas detection system of FIG. 24A.

The de-multiplexer 2404 is illustrated in FIG. 24B. The demultiplexer 2404 comprises a sealed chamber 2418 that contains the gas. Pump and Raman signals are introduced into the chamber 2418 by an output end 2410 of the PGB fiber 2403. The pump and Raman signals are collimated by a collimating lens 2413. The Raman signal 2419 passes through filter 2415, which is designed to reflect the pump light. This Raman signal 2419 is focused by a lens 2414 onto the fiber 2411 that directs the light to the tunable filter or monochromator 2406. The pump light 2417 is reflected by the filter 2415 onto a detector 2416 for power monitoring. The multiplexer 2420 is similar to that shown in FIG. 22B.

Optical connection is provided between the optical components as shown in FIGS. 22A, 23A, and 24A although structures may be included between these optical components as well. A variety of these components may comprise optical fiber or optical fiber devices.

The systems and components shown in FIGS. 22A-22C, 23A-22C, and 24A-24B are examples only. One skilled in the art may devise alternative configurations and designs. For example, the filter 2316 shown in FIG. 23B can be designed to reflect the pump light and pass the signal. The fiber positions may be different in such an embodiment. Similarly, the filter 2415 in FIG. 24B can be designed to reflect the Raman signal. Fiber positions may likewise be different. The pump monitoring functions in FIGS. 23C and 24B can be eliminated. Fibers used to carry light to filters and detectors in FIGS. 22B, 22C, 22B, 22C, and 24B can also be eliminated by using bulk optics. Alternatively, optical fibers can be used to guide the light. In some embodiments, the PBGF ends can be sealed while gas can enter and exit the core of the PBGF through holes drilled on the side of the fiber. In fact, many holes can be drilled along the fiber to speed gas flow and make gas uniformly distributed along the PBGF. In certain embodiments, however, gas enters and/or exits the PBGF through one or both endfaces.

Other variations are also possible. Additional components can be added to the systems. Likewise, some components in FIGS. 22, 23, and 24 can be omitted and/or locations changed in different embodiments. Other configurations and variations are also possible. The components can also be designed differently. For example, other configurations and designs the multiplexers and demultiplexers may be used. In certain embodiments, one or both the multiplexer or demultiplexer may be excluded. Additionally, in any of the example applications described herein a single continuous PBGF or separate portions of PBGF may be used.

EXAMPLES

Any two dielectric media with different refractive indexes can be used to implement the fiber structures described herein. A suitable candidate for the high index material is glass, especially fused silica glass which is advantageous physical and optical properties, and durability. The low index medium can be chosen from one or a mixture of gases or vacuum. This choice of low index material has high nonlinear threshold, low scattering and absorption loss, and very low dispersion.

A PBGF with a wide transmission band has many applications, e.g. telecommunication and trace gas analysis based on spectral absorption or Raman scattering techniques. Such a broad transmission band can be achieved in Bragg fibers with $v<\pi$, i.e. $d<0.5\lambda/(n_h^2-n_l^2)^{1/2}$ and $R<0.3$. Wavelength scaling enables fiber designs for any wavelength range. The fiber dimension can be scaled proportionally to wavelength, i.e. double wavelength results in double fiber dimension.

Broad transmission band can also be achieved by reducing the average thickness, d, in any cladding design which resembles a layered cladding structure around a core. In certain embodiments comprising a triangularly stacked structure where reduced average d is used to achieve a 200 nm transmission band, $v<\pi$ and $R<0.05$. In the circularly stacked structure described in FIG. 4, for example, a 200 nm transmission band can be achieved with $v<\pi$, i.e. $d<0.5\lambda/(n_h^2-n_l^2)^{1/2}$ and $R<0.2$.

Low transmission loss is also advantageous for a range of applications. Loss can be reduced or minimized by operating at $v_{opt}$ determined by equation 7. In certain embodiments, the average thickness, d may be used to estimate $v_{opt}$, in case where d varies circumferentially. For example, for $R=0.2$, $v_{opt} \approx 0.7\pi$ for m=1, $1.60\pi$ for m=2, and $2.56\pi$ for m=3. For $R=0.1$, $v_{opt} \approx 0.67\pi$ for m=1, $1.58\pi$ for m=2, and $2.55\pi$ for m=3.

Low dispersion is also useful for telecommunications. In certain embodiments, core radius can be chosen to be larger than 10 μm to achieve dispersion below 20 ps/nm/km. In addition, the first layer thickness, δ, and refractive indices can be varied to tailor dispersion. The first layer thickness δ can be adjusted from 1% to 50% of d. In some embodiments, for example, $\delta(n_h^2-n_l^2)^{1/2}/\lambda=0.01$ to 2 can be used to tailor dispersion. A large d can be used to achieve strong negative dispersion. For robust single mode operation, core radius ρ may be smaller than 15 μm in certain embodiments.

It may be useful for broad band transmission band to eliminate surface modes on the core/cladding boundary. In various embodiments, the $\delta(n_h^2-n_l^2)^{1/2}/\lambda$ of the core/cladding boundary may be less than about 0.15 for a complete elimination of surface modes. The reduction of the first layer thickness will decrease confinement and increase mode penetration into the first layer, which leads to higher confinement loss and scattering loss from the first layer. In practice, a compromise between surface mode loss and confinement/scattering loss has to be sought.

Other embodiments having different designs and configurations are possible and should not be limited to those described above. Moreover, the above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the scope of the invention, as defined by the appended claims, and equivalents thereof.

What is claimed is:

1. A gas analyzer comprising:
   a light source;
   an optical fiber optically coupled to said light source, said optical fiber comprising a core and a cladding, said cladding comprising a first plurality of ring-shaped regions defined by high index material having an index of refraction, $n_h$, and a second plurality of ring-shaped regions having a low index of refraction, $n_l$, said first plurality of high index ring-shaped regions having an average thickness, d, and an average periodicity, $\Lambda$, said optical fiber further comprising one or more holes in said core or in proximity to said core for receiving a gas, said optical fiber having a sufficient interaction length such that an interaction of said gas with light from said source causes Raman scattering within said fiber and propagation of Raman-scattered light within said optical fiber; and
   at least one optical detector configured to receive the Raman-scattered light and identify and/or quantify the gas.

2. The gas analyzer of claim 1, wherein said optical fiber comprises a photonic bandgap fiber.

3. The gas analyzer of claim 2, wherein said core has a width larger than about 10 μm.

4. The gas analyzer of claim 1, wherein said optical fiber further comprises openings in sides thereof to allow gas flow in and out of said holes in said fiber.

5. The gas analyzer of claim 1, further comprising at least one optical and gas multiplexer configured to combine light from the light source and the gas.

6. The gas analyzer of claim 5, further comprising at least one optical and gas demultiplexer configured to separate light propagating in the fiber and the gas.

7. The gas analyzer of claim 6, further comprising a reflective narrow band filter disposed so as to separate light from the light source and Raman-scattered light.

8. The gas analyzer of claim 6, wherein said detector is arranged to measure the Raman-scattered light to identify or quantify the gas, or both.

9. The gas analyzer of claim 8, wherein said detector is arranged to measure a backward-propagating Raman-scattered light.

10. The gas analyzer of claim 8, wherein said detector is arranged to measure a forward-propagating Raman-scattered light.

11. The gas analyzer of claim 1, wherein said Raman scattering comprises stimulated Raman scattering.

12. The gas analyzer of claim 1, wherein the core is hollow and the fiber is configured to allow the flow of gas through the hollow core.

13. The gas analyzer of claim 1, wherein a ratio $d/\Lambda$ is less than about 0.3.

14. The gas analyzer of claim 1, wherein a ratio $d/\Lambda$ is less than about 0.2.

* * * * *